(12) United States Patent
Liu et al.

(10) Patent No.: US 6,531,296 B1
(45) Date of Patent: Mar. 11, 2003

(54) NUCLEAR TYROSINE KINASE RAK

(75) Inventors: Edison T. Liu, Chapel Hill, NC (US);
Rolf J. Craven, Durham, NC (US);
William G. Cance, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 08/492,723

(22) Filed: Jun. 20, 1995

(51) Int. Cl.[7] ................. C07K 14/435; C12N 5/10; C12N 15/11; C12N 15/63
(52) U.S. Cl. ............ 435/69.1; 435/193; 435/194; 435/320.1; 435/325; 530/300; 530/350; 536/23.1
(58) Field of Search ................ 530/300, 350; 536/23.1; 435/320.1, 240.2, 325, 193, 194, 69.1; 424/94.5

(56) References Cited

U.S. PATENT DOCUMENTS 6,326,469 B1 * 12/2001 Ullrich et al.

FOREIGN PATENT DOCUMENTS

WO          9315201      * 8/1993

OTHER PUBLICATIONS

Cance et al.; *Rak, a Novel Nuclear Tyrosine Kinase Expresed in Epithelical Cells,* Cell Growth and Differentiation 5:1347 (1994).

Craven et al.; *The src–related nuclear tyrosine kinase rak associates with Rb, cylin D3 and p34,* AACR abstract 36: A3357 (1995).

Smith, D.B. et al. (1988) Gene 67:31–40.*

Lee, J. et al., *Cloning of FRK, a novel human intracellular Src–like tyrosine kinase encoding gene,* Gene 138:247–251 (1994).

Cance, W. G. et al., *Novel Protein Kinase Expressed in Human Breast Cancer,* Int. J. Cancer 54:571–577 (1993).

* cited by examiner

Primary Examiner—Michael Pak
(74) Attorney, Agent, or Firm—Myers Bigel Sibley and Sajovec

(57) ABSTRACT

A nuclear tyrosine kinase called Rak has been identified. This tyrosine kinase is expressed primarily in epithelial cells, and has been found to be a growth inhibiting kinase. Domains of the Rak protein, and corresponding peptides, have been found to inhibit CDC2 function and therefore block the cell cycle and inhibit cell growth. A domain of the Rak protein which binds to the retinoblastoma gene product has also been identified, and is in a domain distinct from the CDC2 binding region. Peptides which bind to CDC2, and peptides which bind to the retinoblastoma gene product, are described.

8 Claims, 8 Drawing Sheets

```
  1                                                        TTTT
  5   AATTTTATTTTATTTTTGTTGTGGGATTCTTAAGCAGATAAGAAG
 50   AAAAGACACCTTCCTAGTGAGCAGCTGCCCAGCTCCTGCTCAGTT
 95   TTGCCTCGGGGTAGCACCTCCAGCCACAGAAAGCAAGCCGGTAAG
140   TCTCTCCAGGTAGGACTTGCTGCAACCCCAGCTCCTGCTCAGTTT
185   TGCCTCGGGGTTAGCACCTTCCAGCCACAGAACGAAGCCGGTAGT
230   CTCTCAGTAGACTTGGTGCAACCCAGCTGCTGGACTGATCTGAAA
275   CGGACTTTGCATACTCTCCGAAGTATGGTGAGTTGGTGCTGACTT
320   CAAAGTTGCCTGGTGAACCAAGATAAGGTGGATCGCAGAGACTAA
365   GGGGAGAGGGAGAAGCCCTGCTCCTCTTCTCCCCACCAAGGCACA
410   ATGAGCAACATCTGTCAGAGGCTCTGGGAGTACCTAGAACCCTAT
  1    M   S   N   I   C   Q   R   L   W   E   Y   L   E   P   Y

CTCCCCTGTTTGTCCACGGAGGCAGACAAGTCAACCGTGATTGAA
 16    L   P   C   L   S   T   E   A   D   K   S   V   I   E

AATCCAGGGGCCCTTTGCTCTCCCCAGTCACAGAGGCATGGCCAC
 31    N   P   G   A   L   C   S   P   Q   S   Q   R   H   G   H

TACTTTGTGGCTTTGTTTGATTACCAGGCTCGGACTGCTGAGGAC
 46    Y   F   V   A   L   F   D   Y   Q   A   R   T   A   E   D

TTGAGCTTCCGAGCAGGTGACAAACTTCAAGTTCTGGACACTTTG
 61    L   S   F   R   A   G   D   K   L   Q   V   L   D   T   L

CATGAGGGCTGGTGGTTTGCCAGACACTTGGAGAAAAGACGAGAT
 76    H   E   G   W   W   F   A   R   H   L   E   K   R   R   D   SH3

GGCTCCAGTCAGCAACTACAAGGCTATATTCCTTCTAACTACGTG
 91    G   S   S   Q   Q   L   Q   G   Y   I   P   S   N   Y   V

GCTGAGGACAGAAGCCTACAGGCAGAGGCGTGGTTCTTTGGAGCA
106    A   E   D   R   S   L   Q   A   E   A   W   F   F   G   A

ATCAGAAGATCAGATGCAGAGAAACAACTATTATATTCAGAAAAC
121    I   R   R   S   D   A   E   K   Q   L   L   Y   S   E   N

AAGACCGGTTCCTTTCTAATCAGAGAAAGTGAAAGCCAAAAAGGA
136    K   T   G   S   F   L   I   R   E   S   E   S   Q   K   G

GAATTCTCTCTTTCAGTTTTAGATGGAGCAGTTGTAAAACACTAC
151    E   F   S   L   S   V   L   D   G   A   V   V   K   H   Y   SH2

AGAATTAAAAGACTGGATGAAGGGGGATTTTTTCTCACGCGAAGA
166    R   I   K   R   L   D   E   G   G   F   F   L   T   R   R

AGAATCTTTTCAACACTGAACGAATTTGTGAGCCACTACACCAAG
181    R   I   F   S   T   L   N   E   F   V   S   H   Y   T   K

ACAAGTGACGGCCTGTGTGTCAAGCTGGGGAAACCATGCTTAAAG
196    T   S   D   G   L   C   V   K   L   G   K   P   C   L   K

ATCCAGGTCCCAGCTCCATTTGATTTGTCGTATAAAACCGTGGAC
211    I   Q   V   P   A   P   F   D   L   S   Y   K   T   V   D
```

*FIG. 1A*

```
     CAATGGGAGATAGACCGCAACTCCATACAGCTTCTGAAGCGATTG
226  Q  W  E  I  D  R  N  S  I  Q  L  L  K  R  L

GGATCTGGTCAGTTTGGCGAAGTATGGGAAGGTCTGTGGAACAAT
241  G  S  G  Q  F  G  E  V  W  E  G  L  W  N  N

ACCACTCCAGTAGCAGTGAAAACATTAAAACCAGGTTCAATGGAT
256  T  T  P  V  A  V  K  T  L  K  P  G  S  M  D

CCAAATGACTTCCTGAGGGAGGCACAGATAATGAAGAACCTAAGA
271  P  N  D  F  L  R  E  A  Q  I  M  K  N  L  R

CATCCAAAGCTTATCCAGCTTTATGCTGTTTGCACTTTAGAAGAT
286  H  P  K  L  I  Q  L  Y  A  V  C  T  L  E  D

CCAATTTATATTATTACAGAGTTGATGAGACATGGAAGTCTGCAA
301  P  I  Y  I  I  T  E  L  M  R  H  G  S  L  Q

GAATATCTCCAAAATGACACTGGATCAAAAATCCATCTGACTCAA
316  E  Y  L  Q  N  D  T  G  S  K  I  H  L  T  Q

CAGGTAGACATGGCGGCACAGGTTGCCTCTGGAATGGCCTATCTG
331  Q  V  D  M  A  A  Q  V  A  S  G  M  A  Y  L

GAGTCTCGGAACTACATTCACAGAGATCTGGCTGCCAGAAATGTC
346  E  S  R  N  Y  I  H  R  D  L  A  A  R  N  V

CTCGTTGGTGAACATAATATCTACAAAGTAGCAGATTTTGGACTT
361  L  V  G  E  H  N  I  Y  K  V  A  D  F  G  L

GCCAGAGTTTTTAAGGTAGATAATGAAGACATCTATGAATCAAGA
376  A  R  V  F  K  V  D  N  E  D  I  Y  E  S  R

CACGAAATAAAGCTACCGGTGAAGTGGACTGCGCCCGAAGCCATT
391  H  E  I  K  L  P  V  K  W  T  A  P  E  A  I

CGTAGTAATAAATTCAGCATTAAGTCCGATGTATGGTCATTTGGA
406  R  S  N  K  F  S  I  K  S  D  V  W  S  F  G

ATCCTTCTTTATGAAATCATTACTTATGGCAAAATGCCTTACAGT
421  I  L  L  Y  E  I  I  T  Y  G  K  M  P  Y  S

GGTATGACAGGTGCCCAGGTAATCCAGATGTTGGCTCAAAACTAT
436  G  M  T  G  A  Q  V  I  Q  M  L  A  Q  N  Y

AGACTTCCGCAACCATCCAACTGTCCACAGCAATTTTACAACATC
451  R  L  P  Q  P  S  N  C  P  Q  Q  F  Y  N  I

ATGTTGGAGTGCTGGAATGCAGAGCCTAAGGAACGACCTACATTT
466  M  L  E  C  W  N  A  E  P  K  E  R  P  T  F

GAGACACTGCGTTGGAAACTTGAAGACTATTTTGAAACAGACTCT
481  E  T  L  R  W  K  L  E  D  Y  F  E  T  D  S
```

FIG. 1B

```
     TCATATTCAGATGCAAATAACTTCATAAGATGAACACTGGAGAAG
496  S  Y  S  D  A  N  N  F  I  R  *  (SEQ ID NO:2)
     AATATCAAATAATAAAGTAGCAAAACAAATTCAAATAATAATCCA
     TTCCAAAATACAATGTTATCAACCAACTGCACAATCAGTTTATCC
     TGACATATTCAAGTGATAGGATAAAGTTGGCCATGTATTATGAAA
     AAGATTATTTGTGCATTTTATTGACTGGGCAACACTGCAGGACAG
     TCAAGGTGATATATAATTTCCTCACTGCCTGGTAAAATTAAGCAC
     ACTAAACCAAGTTATTTTTCTTTTTAAGAGATACTTACATTTCCA
     TTTATTGTTTGAAATGTCGATCAAGAGAATCAACAGATGATAGTC
     CAATTTTTACTCAGTGACTGTTGTAGCATTTTCCTGTTTACTGAT
     TAGAGTGGTTATCATTATTCCTCAGATTGCTGAATCCCATCAGGC
     TGTTATTATGAAGGAATTTGATTGCTTTGCTGCACAGCAGGACCT
     GTGCTTTGAGATTTTTTTTTCTCTTTTAAAATATCCTGTAACTAC
     AATGATGGTAAAGCCATGTTAAATGACTTGATTGTACTTGGAGTA
     ATTGCACATTTTTTTTCTATGCATAAAAAAATGATGCAGCTGTTG
     AGAAAACGAAGTCTTTTTCATTTGCAGAAGGAAATGATGGAATT
     TTTCTGTACTTCAGTATGTGTCAACTGAGAGTCATATACATTAGT
     TTTAATCTCTTAATATTGAGAATCAGGTTGCAAACGGATGAGTTA
     TTATCTATGAAATGTGAGAAATGTCTAATAGCCCATAAGTCTGAG
     AAATAGGTATCAAAATAGTTTAGGAAAATGAGAGGAGAACAGTAG
     GATTGCTGTGGCCTAGACTTCTGGTAATTAATAAGAAAAGAAG
     TACCCTTTGGCCTACAAAAAAAAAAAAAAAAG (SEQ ID NO:1)
```

FIG. 1C

```
RAK   1 MSNICQR........................................L
STK   1 MGPCCSKQTKALNNQPDKSKSK.....................DVV
SRC   1 MGSNKSKPKDASQRRRSLEPAENVHGAGGGAFPASQTPSKPASADGHRGP
LYN   1 MGCIKSKGKD................SLSDDGVDLKTQPVRNTER
FYN   1 MGCVQCKDKE..ATKLTDERDNSLTQSLGYRYGTDPTPQHYPSFTVTTIP
LCK   1 MGCGCSSHPE.................DDWMENIDVCENCHYPI
ABL   1 MLEICLKLVGCKSKK...............GLSSSSSCYLEE

RAK   9 WEYLEPYLPCLSTEADKSTVIENPGALCSPQSQRHGHYFVALFDYQARTA
STK  26 LKENTSPFSQNTNNIMHVSHNQPPNINPPMLGGPGVTIFVALYDYEARIS
SRC  51 SAAFAPAAAEPKLFGGFNSSDTVTSPQRAGPLAGGVTTFVALYDYESRTE
LYN  30 TIYVRDPTSNKQQRPVPESQLLPGQRFQTKDPEEQGDIVVALYPYDGIHP
FYN  49 NYNNFHATAGQGLTVFGGVNSSSHTGTLRTRGGTGVTLFVALYDYEARTE
LCK  28 VPLDGKGTLLIRNGSEVRDPLVTYEGSNPPASPLQDNLVIALHSYEPSHD
ABL  28 ALQRPVASDFEPQGLSEAARWNSKENLLAGPSENDPNLFVALYDFVASGD

RAK  59 EDLSFRAGDKLQVLDTLHEG.WWFARHLEKRRDGSSQQLQGYIPSNYVAE
STK  76 EDLSFKKGERLQIINTA.DGDWWYARSLI......T.NSEGYIPSTYVAP
SRC 101 TDLSFKKGERLQIVNNT.EGDWWLAHSL......ST.GQTGYIPSNYVAP
LYN  80 DDLSFKKGEKMKVLEEH..GEWWKAKSLL......T.KKEGFIPSNYVAK
FYN  99 DDLSFQKGEKFQILNSS.EGDWWEARSL......TT.GGTGYIPSNYVAP
LCK  78 GDLGFEKGEQLRILEQS..GEWWKAQSL......TT.GQEGFIPFNFVAK
ABL  78 NTLSITKGEKLRVLGYNHNGEWCEAQT.........KNGQGWVPSNYITP

RAK 108 DRSLQAEAWFFGAIRRSDAEKQLLYSENKTGSFLIRESESQKGEFSLSVL
STK 118 EKSYEAEEWYFGDVKRAEAEKRLMVRGLPSGTFLIRKAETAVGNFSLSVR
SRC 143 SDSIQAEEWYFGKITRRESERLLLNAENPRGTFLVRESETTKGAYCLSVS
LYN 121 LNTLETEEWFFKDITRKDAERQLLAPGNSAGAFLIRESETLKGSFSLSVR
FYN 141 VDSIQAEEWYFGKLGRKDAERQLLSFGNPRGTYLIRESETTKGAYSLSIR
LCK 119 ANSLEPEPWFFKNLSRKDAERQLLAPGNTHGSFLIRESESTAGSFSLSVR
ABL 119 VNSLEKHSWYHGPVSRNAAE.YLLSSGIN.GSFLVRESESSPGQRSISLR

RAK 158 D.....GAVVKHYRIKRLDEGGFFLTRRRIFSTLNEFVSHYTKTSDGLCV
STK 168 D.....GDSVKHYRVRKLDTGGYFITTRAPFNSLYELVQHYTKDADGLVC
SRC 193 DFDNAKGLNVKHYKIRKLDSGGFYITSRTQFNSLQQLVAYYSKHADGLCH
LYN 171 DFDPVHGDVIKHYKIRSLDNGGYYISPRITFPCISDMIKHYQKQADGLCR
FYN 191 DWDDMKGDHVKHYKIRKLDNGGYYITTRAQFETLQQLVQHYSERAAGLCC
LCK 169 DFDQNQGEVVKHYKIRNLDNGGFYISPRITFPGLHELVRHYTNASDGLCT
ABL 169 YE....GRV.YHYRINTASDGKLYVSSESRFNTLAELVHHHSTVADGLIT

RAK 203 KLGKPCLKIQVPAPFDLSYKTVDQWEIDRNSIQLLKRLGSGQFGEVWEGL
STK 213 ALTLPCPKDKPVTGGIA....KDAWEIPRESLRLNRKLGAGQFGEVWAGV
SRC 243 RLTTVCPTSKPQTQGLA....KDAWEIPRESLRLEVKLGQGCFGEVWMGT
LYN 221 RLEKACISPKPQKPWD.....KDAWEIPRESIKLVKRLGAGQFGEVWMGY
FYN 241 RLVVPCHKGMPRLTDLSVKT.KDVWEIPRESLQLIKRLGNGQFGEVWMGT
LCK 219 RLSRPCQTQKPQKP.....WWEDEWEVPRETLKLVERLGAGQFGEVWMGY
ABL 212 TLHYPAPKRNKPTVYGVSPN.YDKWEMERTDITMKHKLGGGQYGEVYEGV
```

*FIG. 2A*

```
RAK 253 WNNTT.PVAMKTLKPGSMDPNDFLREAQIMKNLRHPKLIQLYAVCTLEDP
STK 259 WNNTT.QVAMKTLKPGTMSPASFLDEAGVMKKLRHKHLVQLYAICSDREP
SRC 289 WNGTT.RVAIKTLKPGTMSPEAFLQEAQVMKKLRHEKLVQLYAVVS.EEP
LYN 266 YNNST.KVAMKTLKPGTMSVQAFLEEANLMKTLQHDKLVRLYAVVTREEP
FYN 290 WNGNT.KVAIKTLKPGTMSPESFLEEAQIMKKLKHDKLVQLYAVVS.EEP
LCK 264 YNGHT.KVAMKSLKQGSMSPDAFLAEANLMKQLQHQRLVRLYAVVT.QEP
ABL 261 WKKYSLTVAMKTLKEDTMEVEEFLKEAAVMKEIKHPNLVQLLGVCTREPP

RAK 302 IYIITELMRHGSLQEYLQNDTGSKIHLTQQVDMAAQVASGMAYLESRNYI
STK 308 IYIVTEYMSGGSLLDYLSKGEGVNLQLPTLIDMAAQVASGMAFLEAQGYI
SRC 337 IYIVTEYMSKGSLLDFLKGETGKYLRLPQLVDMAAQIASGMAYVERMNYV
LYN 315 IYILTEYMAKGSLLDFLKSDEGGKVLLPKLIDFSAQIAEGMAYIERKNYI
FYN 338 IYIVTEYMSKGSLLDFLKDGEGRALKLPNLVDMAAQVARGMAYIERMNYI
LCK 312 IYILTEYMENGSLVDFLKTPSGIKLTINKLLDMAAQIAEGMAFIEERNYI
ABL 311 FYIITEFMTYGNLLDYLRECNRQEVNAVVLLYMATQISSAMEYLEKKNFI

RAK 352 HRDLAARNVLVGEHNIYKVADFGLARVFKVDNEDIYESRHEIKLPVKWTA
STK 358 HRDLAARNILVGENYICKVADFGLARL...IEDDEYTAHEGAKFPIKWTA
SRC 387 HRDLRAANILVGENLVCKVADFGLARL...IEDNEYTARQGAKFPIKWTA
LYN 365 HRDLRAANVLVSESLMCKIADFGLARV...IEDNEYTAREGAKFPIKWTA
FYN 388 HRDLRSANILVGNGLICKIADFGLARL...IEDNEYTARQGAKFPIKWTA
LCK 362 HRDLRAANILVSDTLSCKIADFGLARL...IEDNEYTAREGAKFPIKWTA
ABL 361 HRDLAARNCLVGENHLVKVADFGLSRL...MTGDTYTAHAGAKFPIKWTA

RAK 402 PEAIRSNKFSIKSDVWSFGILLYEIITYGKMPYSGMTGAQVIQMLAQNYR
STK 405 PEAALYNRFTIKSDVWSFGILMAEIVTKGRIPYPGMTNAQTIAEVEKGYR
SRC 434 PEAALYGRFTIKSDVWSFGILLTELTTKGRVPYPGMVNREVLDQVERGYR
LYN 412 PEAINFGCFTIKSDVWSFGILLYEIVTYGKIPYPGRTNADVMTALSQGYR
FYN 435 PEAALYGRFTIKSDVWSFGILLTELVTKGRVPYPGMNNREVLEQVERGYR
LCK 409 PEAINYGTFTIKSDVWSFGILLTEIVTHGRIPYPGMTNPEVIQNLERGYR
ABL 408 PESLAYNKFSIKSDVWAFGVLLWEIATYGMSPYPGIDLSQVYELLEKDYR

RAK 452 LPQPSNCPQQFYNIMLECWNAEPKERPTFETLRWKLEDYF.ETDSSYSDA
STK 455 MPIMPGCPEPLYNIMLQTWNKDPENRPTFDYLQGVLEDYFVSTEQGYRDL
SRC 484 MPCPPECPESLHDLMCQCWRKEPEERPTFEYLQAFLEDYFTSTEPQYQPG
LYN 462 MPRVENCPDELYDIMKCWKEKAEERPTFDYLQSVLDDFYTATEGQYQQQ
FYN 485 MPCPQDCPISLHELMLNCWKKDPEERPTFEYLQGFLEDYFTATEPQYQPG
LCK 459 MVRPDNCPEELYQLMRLCWKERPEDRPTFDYLRSVLEDFFTATEGQYQPQ
ABL 458 MERPEGCPEKVYELMRACWQWNPSDRPSFAEIHQAFETMFQ..ESSISDE

RAK 501 NNFIR  (SEQ ID NO:2)
STK 505 GEANS  (SEQ ID NO:X)
SRC 534 ENL    (SEQ ID NO:X)
LYN 512 P      (SEQ ID NO:X)
FYN 353 DNL    (SEQ ID NO:X)
LCK 509 P      (SEQ ID NO:X)
ABL 506 VEK    (SEQ ID NO:X)
```

*FIG. 2B*

FIG. 8
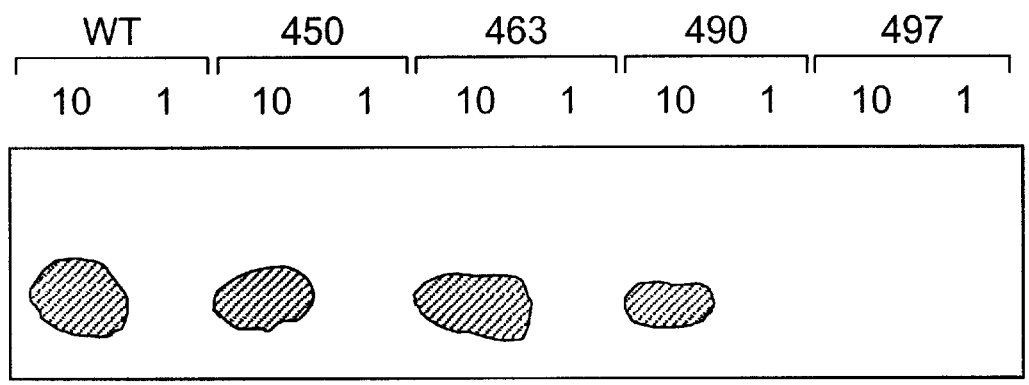
FIG. 9A  FIG. 9B
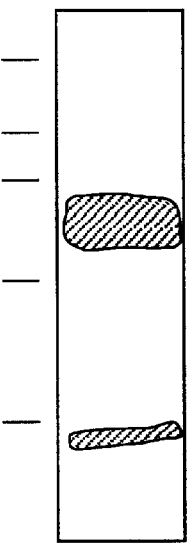 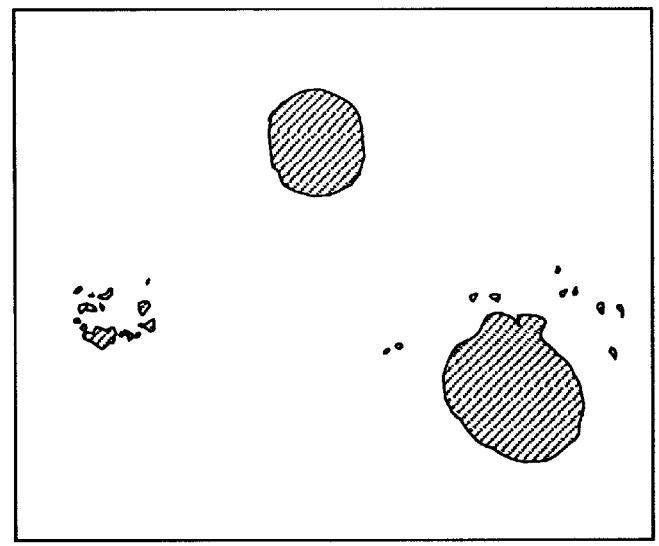
FIG. 9C
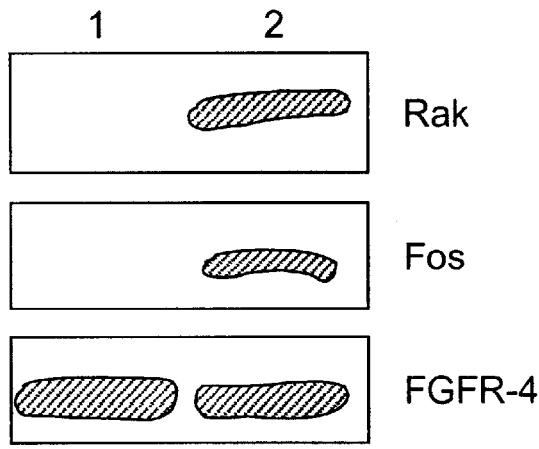

NUCLEAR TYROSINE KINASE RAK

This invention was made with government support under Grant No. CA01625/CA58233 awarded by the National Institutes of Health. The government has certain rights in the invention.

This work was supported by government grants. The government may have certain rights to this invention.

FIELD OF THE INVENTION

The present invention relates to a nuclear tyrosine kinase called Rak which is expressed primarily in epithelial cells. Rak has been found to be a growth inhibiting kinase. Domains of the Rak protein, and corresponding peptides, have been found to inhibit CDC2 function and therefore block the cell cycle and inhibit cell growth. Rak protein also binds to the retinoblastoma gene product in a domain distinct from the CDC2 binding region.

BACKGROUND OF THE INVENTION

The protein tyrosine kinases are a related family of proteins that play a pivotal role in signal transduction and the regulation of cellular proliferation and have been linked to tumorigenesis through both over expression and mutation. Tyrosine kinases are frequently divided into three groups: the transmembrane receptors, such as the growth factor receptors; the cytoplasmic tyrosine kinases, which are thought to act as internal transmitters of growth signals from the cell membrane; and the nuclear tyrosine kinases thought to be involved in the direct regulation of cellular division.

Prototypes of the various tyrosine kinase subfamilies include HER-2/neu, a receptor tyrosine kinase whose overexpression is a powerful predictor of poor prognosis in breast cancer; the focal adhesion kinase (FAK), a cytoplasmic kinase which plays a central role in cellular adhesion; and abl, a nuclear tyrosine kinase that is an inhibitor of cellular growth and that, when rearranged by translocation, is etiologic for chronic myelogenous leukemia.

All tyrosine kinases function as molecular "switches" for critical cellular functions such as growth, differentiation, and even cell death. These molecular switches act by physically interacting with other molecules, first by binding, which is often followed by phosphorylation, whereby the kinase adds a phosphate group to the substrate molecule. These chemical chain reactions are the connections through which a signal can be transmitted through a kinase in to the nucleus. Thus knowledge of these potentially intricate interactions may permit the targeted disruption of vital biochemical pathways of a cancer cell, or may be used as diagnostic markers of disease virulence.

SUMMARY OF THE INVENTION

A first aspect of the present invention is a peptide having the amino acid sequence Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser (SEQ ID NO: 3), or the sequence Lys-Arg-Arg-Asp-Gly-Ser-Ser-Gln-Gln-Leu-Gln (SEQ ID NO:4).

A further aspect of the present invention is a fusion protein comprising a peptide having the sequence Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser (SEQ ID NO: 3) or a peptide having the sequence Lys-Arg-Arg-Asp-Gly-Ser-Ser-Gln-Gln-Leu-Gln (SEQ ID NO:4).

A further aspect of the present invention is a method of inhibiting CDC2 function within a cell by administering a peptide having the amino acid sequence Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser (SEQ ID NO: 3) or Lys-Arg-Arg-Asp-Gly-Ser-Ser-Gln-Gln-Leu-Gln (SEQ ID NO:4).

A further aspect of the present invention is a method of synchronizing a plurality of cells so that a majority of cells exhibit the same phase of the cell cycle, where the cells are administered a peptide of sequence Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser) (SEQ ID NO: 3) or sequence Lys-Arg-Arg-Asp-Gly-Ser-Ser-Gln-Gln-Leu-Gln (SEQ ID NO:4).

A further aspect of the present invention is a method of inhibiting cell proliferation by administering to the cell a peptide of amino acid sequence Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser (SEQ ID NO: 3); or sequence Lys-Arg-Arg-Ser-Gln-Gln-Leu-Gln (SEQ ID NO:4), the peptide administered in an effective cell proliferation inhibitory amount.

BRIEF DESCRIPTION OF THE DRAWINGS

FIG. 1 shows the cDNA sequence (SEQ ID NO: 1) and predicted amino acid sequence (SEQ ID NO: 2) of Rak. The SH3 domain (amino acids 47–108) is singly underlined and the SH2 domain (amino acids 116–198) is doubly underlined. The nuclear localization sequence (amino acids 168–181) and the COOH-terminal regulatory tyrosine (Y497) are shown in bold.

FIG. 2 is a comparison of Rak amino acid sequence (SEQ NO: 2) with the most closely related Src family members and Abl. With the exception of STK, which is a kinase from a lower organism, only the human sequences are shown. Regions of identity are highlighted in bold. Only the first 508 amino acids of the Abl protein are shown and represent the sequence of the type I, unmyristilated Abl isoform.

FIG. 8 shows phosphorylation of $p54^{rak}$ by CSK. In vitro kinase assays were performed on a fusion protein containing the 62 carboxy-terminal amino acids of $p54^{rak}$ and on mutated forms of these peptides in which one of the four tyrosines in this region (Y450, Y463, Y490 and Y497) had been changed to phenylalanine. The peptides were incubated with 10 or 1 ng of CSK purified from baculovirus, electrophoresed on 15% SDS PAGE gels and exposed to film.

FIG. 9A is a Western blot showing $p54^{rak}$ expression in COS7 cells stained with the VH55 antibody. The molecular weight markers are 206, 105, 71, 44 and 29 kDa, from top to bottom respectively.

FIG. 9B shows immunofluorescence of $ps54^{rak}$ in COS7 cells, demonstrating nuclear localizatin in most of the cells. Preimmune controls demonstrated no immunoreactivity (data not shown).

FIG. 9C shows subcellular fractionation of COS7 cells. The cells were lysed in 0.15% Triton X-100 anbd centrifuged. The supernatant contained the cytoplasmic and cellular membrane proteins (Lane 1), and the pellet contained the nuclear fraction. The nuclei were then lysed in a 1% Triton X-100 solution (Lane 2). These fractions were subsequently analyzed by Western blots for $p54^{rak}$, the nuclear protein, c-Fos, and the transmembrane receptor FGFR-4.

DETAILED DESCRIPTION OF THE PREFERRED EMBODIMENTS

Figure 3A:
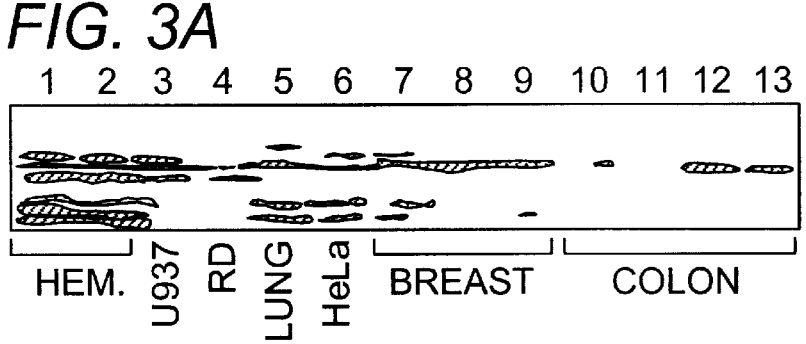
FIG. 3A shows expression and tyrosine kinase activity of p54$^{rak}$ in human cell lines. The thirteen cell lines tests are: Lane 1, K562; Lane 2, HL60; Lane 3, U937; Lane 4, rhabdomyosarcoma; Lane 5, A549; Lane 6, HeLa; Lane 7, 600 PEI; Lane 8, BT20; Lane 9, MCF7; Lane 10, colo205; Lane 11, LS174T; Lane 12, LS180; and Lane 13, HT29. Each lane contained 30 µg of protein and the antibody used was VH55. There was no reactivity with preimmune serum, and immunoreactivity was abrogated with the addition of free Rak peptide.

The cell cycle is a process controlled by a number of cyclin dependent kinases including cdc2, cdk2, cdk4, cdk6 and cdk7. The cdc/cdk proteins are operative at specific points in the cell cycle, providing check-points for control of cell proliferation. CDC2 and its cognate cyclin (B1) are involved in the transition through the Gap2/Mitosis (G2/M) stage of cell growth. Negative control of the cdc/cdks is through natural inhibitors such as p21/p27, and p15/p16. It is known that mutations in the p53 gene prevent expression of the natural cdk inhibitor, p21, resulting in unchecked growth and tumor formation. In addition, aberrations of the cdk inhibitor p16 are common in melanomas, leukemias, and other carcinomas.

The present inventors have determined that the Rak gene product inhibits CDC2 function and thereby interferes with cell growth. The present inventors have further identified the domain of the Rak protein which inhibits CDC2 function as measured by CDC2-induced phosphorylation of histone H1, and that fragments of this domain, (such as an 11-amino acid peptide Lys-Arg-Arg-Asp-Gly-Ser-Ser-Gln-Gln-Leu-Gln (SEQ ID NO:4)) are capable of blocking CDC2 function. This inhibition of CDC2 enzymatic activity will have significant effects on the cell cycle, resulting in a block to cellular proliferation. Chemical peptidomimetics or peptide analogs can also be synthesized with this CDC2 blocking function, based on the inhibitory peptides identified. As used herein, inhibition of CDC2 function means a decrease in the function of CDC2 as compared to a control sample. CDC2 function may be assessed by a variety of means, such as by measuring the phosphorylation of histone H1. An effective CDC2 inhibitory amount of a compound refers to that amount which results in decreased CDC2 activity, compared to a control sample not treated with said compound.

The present peptides and analogs thereof may then be used therapeutically, where it is desired to decrease or inhibit cell proliferation. As used herein, a decrease or inhibition of cellular proliferation due to a stated treatment is assessed compared to the rate of cellular proliferation seen in a control group of cells which is not subjected to said treatment. An effective cell proliferation inhibiting amount of a compound, as used herein, refers to an amount of a compound which decreases cellular proliferation compared to the rate of cellular proliferation seen in an untreated sample of cells. Decreasing cellular proliferation is desirable in the treatment of cancer or other neoplastic conditions, as well as in non-cancerous proliferative diseases. Rak peptides of the present invention, and analogs or mimetics thereof, may thus be used as antineoplastics to block tumor cell growth. Further, as alterations of the cell cycle have been shown to alter the sensitivity of cancerous cells to standard chemotherapeutic agents, Rak peptides of the present invention may be used in combination with standard chemotherapeutic agents.

As the peptides of the present invention, and analogs thereof, inhibit CDC2 function and thereby interfere with the cell cycle, these peptides may further be utilized in cytogenetics to synchronize cells and thus may be used to improve resolution in cytogenetic cell studies. As used herein, the synchronization of a plurality of cells means that a majority (at least 50%, more preferably at least 60%, and most preferably at least, 70, 80, 90 or even 95%) of said plurality of cells exhibit the same stage of the cell cycle.

In addition, the inhibitory effects of RAK on CDC2 function and on cellular growth indicate that mutations altering RAK binding or activity may be permissive for tumor growth. Somatic mutations in RAK may predict for clinical outcome, and germline mutations in RAK could define a cancer susceptibility syndrome. In such cases, RAK would function as a diagnostic.

Peptides of the present invention which bind to the retinoblastoma (rb) gene product may be immobilized on a solid support for collecting and purifying the retinoblastoma gene product. Immobilized peptides may be used in conjunction with antibodies specific for the rb gene product to provide an immunoassay for the rb gene product. This will be useful in assessing soft tissue tumors such as sarcomas, where the absence of the rb gene product is indicative of a more aggressive clinical course. Immunoassay techniques suitable for such an assay are well-known in the art, including techniques for providing positive controls when the absence of an analyte is of interest. Similarly, peptides of the present invention which bind to CDC2 may be immobilized on a solid support for collecting and purifying CDC2, or in an immunoassay to detect the presence of CDC2. The peptides of the present invention may further serve as molecular weight markers.

The peptides of the present invention are those fragments of the RAK protein (SEQ ID NO:2) which bind to CDC2, and those which bind to the retinoblastoma gene product. The peptides of the present invention may further inhibit the activity of the proteins (CDC2 and rb gene product) to which they bind. Peptides of the present invention include but are not limited to peptides consisting of amino acids 1–155 of the RAK protein (SEQ ID NO:2), amino acids 1–152 of the RAK protein (SEQ ID NO:2), amino acids 1–130 of the RAK protein (SEQ ID NO:2), amino acids 1–110 of the RAK protein (SEQ ID NO:2); amino acids 47–108 of the RAK protein (SEQ ID NO:2), amino acids 87–110 (SEQ ID NO:3) of the RAK protein, and a peptide of SEQ ID NO:4.

The present inventors have identified a new tyrosine kinase, Rak (a Russian word for cancer), from human breast cancer cells. Rak shares 51% identity with c-Src. Sequencing of the full-length complementary DNA (SEQ ID NO: 1) reveals that Rak is a tyrosine kinase with a molecular weight of 54,000 (p54) that contains SH2 and SH3 domains that function specifically in protein-protein interactions), as well as tyrosine residues analogous to the autophosphorylation and regulatory tyrosines of the Src family. Biochemical and site-directed mutagenesis analyses revealed that a carboxy-terminal peptide of p54$^{rak}$ is phosphorylated by a cytoplasmic tyrosine kinase (CSK) at the COOH-terminal tyrosine similar to other src-like kinases. However, some properties of Rak are distinct from other members of the Src family: (a) expression of Rak is predominantly in epithelial-derived cell lines and tissues, especially normal liver and kidney, and cell lines of breast and colon origin; (b) Rak does not harbor the NH$_2$-terminal glycine essential for myristylation and membrane localization, moreover the nuclear localization signal in the SH2 domain, and confirmatory subcellular fractionation studies reveal that p54$^{rak}$ resides predominantly in the nucleus. Finally, p54$^{rak}$ is overexpressed in subsets of primary human epithelial tumors.

One highly conserved feature of the Src family appears to be their regulation. All of these kinases isolated thus far contain a tyrosine near the COOH terminus, and in several of the kinases, this tyrosine is phosphorylated and leads to an interaction between the COOH-terminal region and the protein's own SH2 and SH3 domains, sterically hindering the active site. The COOH-terminal tyrosine of the Src family kinases Src, Lyn, Lck and Fyn are phosphorylated by the cytoplasmic tyrosine kinase CSK, resulting in a decrease in their kinase activity. The ability to control the activity of Src-related kinases is critical to normal development, since csk-null transgenic mice fail to develop properly and have activated Src family kinases. In the case of Src, any interruption of its negative regulation, whether by mutation of the carboxy terminus, binding Y527 by other proteins (e.g., polyoma middle T or v-Crk), or constitutive dephosphorylation of Y527 by a phosphatase, is capable of transforming cells. That Rak is phosphorylated by CSK further confirms the structural similarities between Rak and Src. Imamato et al., Cell. 73:1117–1124 (1993); Sabe et al., Mol. Cell. Biol. 72:4706–4713 (1992); Zhena et al., Nature (Lond.) 350:336–339 (1993); MacAuley et al., Oncogene 0:117–128 (1993).

As key signaling molecules, the cytoplasmic tyrosine kinases have been linked to a growing number of human cancers, with c-Src being the most well studied. Its viral counterpart, v-Src, is highly transforming through mutations in key regulatory regions, and these mutations can also render the c-src gene transforming. However, the c-Src kinase has also been linked to cancer through overexpression and activation, but not by somatic mutation. This overexpression of c-Src is frequent in colon tumors and is thought to be a determining factor in the severity of the disease Talamonti et al., J. Clin. Invest. 91:53–60 (1993). In addition, c-yes and lck have also been linked to colon cancer. Src is also overexpressed in breast tumors and is activated in cells overexpressing the receptor tyrosine kinase, HER2/neu. Moreover, c-Src binds directly to the activated HER2/neu and the epidermal growth factor receptors through its SH2 domain, and overexpression of Src may potentiate the activation of the HER2/neu signaling pathway.

Given the similarities between the Src family members, other related kinases may also play an important role in breast cancer. The present inventors screened for protein kinases expressed in human breast cancers using PCR$^3$-based cloning techniques. In a search of the breast cancer cell line 600 PEI and a primary breast tumor, novel member of the Src family of tyrosine kinases, TK1 was isolated (Cance et al., J. Cancer 54:571–577 (1993)). Studies suggested that TK1 was expressed predominantly in epithelial cells and was also expressed in primary human epithelial tumors. The present inventors conducted the cDNA cloning and characterization of TK1, herein called Rak (a Russian word for cancer). Unlike the Src-like tyrosine kinases, Rak does not localize to the cell membrane but rather appears in the nuclei of some cells.

The Rak CDNA sequence (SEQ ID NO: 1) shares several similarities with its homologues, Src, Lyn, and STK: single SH2 and SH3 domains, a consensus autophosphorylation site within the kinase domain, and a regulatory tyrosine near the carboxy terminus. These features distinguish Rak from other tyrosine kinases that contain SH2 and SH3 domains, such as abl and CSK, which are not grouped in the Src family. While Abl contains a tyrosine within the kinase domain resembling the Y416 of Src, it lacks the tyrosine at the site analogous to the Y527 of Src, and CSK lacks both of these putative regulatory tyrosine residues. The carboxy-terminal tyrosine is a critical regulatory site for the Src family members and is phosphorylated by CSK, leading to down-regulation of kinase activity (Derxman et al., EMBO J. 11:2919–2924 (1992)) through an interaction with the protein's own SH2 and SH3 domains (Murphy et al., Mol. Cell. Biol. 13:5290–5300 (1993)). The corresponding tyrosine in Rak is also phosphorylated by CSK in vitro.

There are other differences between Rak and other Src family members. First, p54$^{rak}$ appears to be expressed predominantly in epithelial cells, rather than mesenchymal and hematopoietic cells. It is intriguing that the closest homologue of Rak was the Hydra attenuata tyrosine kinase, STK (Busch et al., Mol. Cell. Biol. 9:4141–4151 (1989)), which is also expressed in the epithelial cells of the Hydra and is involved in epithelial regeneration after injury as well as early development in these simple organisms. In addition to its expression pattern, Rak has an $NH_2$-terminal sequence unlike those of the Src family and a putative nuclear localization signal within its SH2 domain. Therefore, while the Src family kinases are thought to be anchored to the cell membrane, $p54^{rak}$ localizes to the nucleus. Other nuclear tyrosine kinases are to be important effectors of cell growth. For example, abl is a negative regulator of cell growth (Sawyer et al., Cell. 77:121–131 (1994)) and when it is localized in the cytoplasm, cells become transformed (Van Eman et al., Cell. 58:669–678 (1989)). abl may also have a role in transcriptional regulation, since it phosphorylates the carboxy terminal domain of RNA polymerase II, and hyperphosphorylation in this domain is correlated with transcription elongation (Baskeran et al., Proc. Nat'l Acad. Sci. USA 90:1167–1171 (1993)). Another nuclear tyrosine kinase, Weel, phosphorylates $p34^{cdc2}$ at Y15, and Weel activity is critical for proper timing of the induction of meiosis following DNA replication.

The placement of a nuclear localization signal within the Rak SH2 domain indicates that Rak could be bound to other tyrosine-phosphorylated proteins or to its own carboxy terminus through its SH2 domain until some signal is transmitted. This could disrupt an association with the Rak SH2 domain, making the nuclear localization signal accessible to recognition by another protein and allowing Rak to traverse the nuclear membrane, where it might phosphorylate a different set of targets. Since $p54^{rak}$ appears to be variably localized to the nucleus and cytoplasm in different cell lines, the proportion of $p54^{rak}$ in the nucleus may modulate its biology.

Amino acid sequences disclosed herein are presented in the amino to carboxy direction, from left to right. The amino and carboxy groups are not presented in the sequence. Amino acid residues are represented herein by three letter code, in accordance with 37 CFR Section 1.822 and established usage. See, e.g., PatentIn User Manual, 99–102 (November 1990) (U.S. Patent and Trademark Office, Office of the Assistant Commissioner for Patents, Washington, D.C. 20231); Genes and Genomes, Singer & Berg (Eds.), University Science Books, Mill Valley, Calif., 1991, at p. 60.

As used herein, a "native DNA sequence" or "natural DNA sequence" means a DNA sequence which can be isolated from a non-transgenic subject's cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art, as long as the DNA molecules produced retain the native DNA sequence. As used herein, a mammalian DNA sequence is that which can be isolated from non-transgenic mammalian cells or tissue. As used herein, a human DNA sequence is a that which can be isolated from non-transgenic human cells or tissue.

A. Inhibitory Analogs and Mimetics

Analogs of the RAK peptides are an aspect of the present invention. As used herein, an "analog" is a chemical compound similar in structure to a first compound (a RAK protein or peptide), and having either a similar or opposite physiologic action as the first compound. With particular reference to the present invention, RAK inhibitory peptide analogs are those compounds which, while not having the amino acid sequences of the native RAK inhibitory peptides (e.g., SEQ ID NO:3 and SEQ ID NO:4) are capable of inhibiting cdc2 and of regulating cell growth in the same manner as the RAK inhibitory peptides. Such analogs may be peptide or non-peptide analogs, including nucleic acid analogs, as described in further detail below.

In protein-protein interactions, the interaction takes place at surface-accessible sites in a stable three-dimensional molecule. By arranging the critical binding site residues in an appropriate conformation, peptides which mimic the essential surface features of the present RAK inhibitory proteins may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, Science, 247, 28029 (1990); Rossmann, Nature, 333, 392–393 (1988); Weis et al., Nature, 333, 426–431 (1988); James et al., Science, 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on the function of the peptides.

Non-peptide mimetics of the peptides of the present invention are also an aspect of this invention. Non-protein drug design may be carried out using computer graphic modeling to design non-peptide, organic molecules able to bind CDC2, or otherwise function as Rak peptides. See, e. g., Knight, BIO/Technology, 8, 105 (1990). Itzstein et al, Nature, 363, 418 (1993) (peptidomimetic inhibitors of influenza virus enzyme, sialidase). Itzstein et al modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al, *Science*, 263, 380 (January 1994) regarding the rational design of bioavailable nonpeptide cyclic ureas that function as HIV protease inhibitors. Lam et al used information from x-ray crystal structure studies of HIV protease inhibitor complexes to design nonpeptide inhibitors.

The modeling of a protein kinase structure using the known structure of other kinases is reported by Knighton et al., *Science*, 258, 130 (1992) (smooth muscle myosin light chain kinase catalytic core modeled using crystallography data of cyclic AMP-dependent protein kinase catalytic subunit and a bound pseudosubstrate inhibitor). See also Marcote et al., *Mol. Cell. Biol.*, 13, 5122 (1993) (crystallography data of cyclic AMP dependent protein kinase used to model Cdc2 protein kinase); Knighton et al., *Science*, 253, 407 (1991); Knighton et al., *Science*, 253, 414 (1991); DeBondt et al., *Nature*, 363, 595 (1993) (crystal structure of human CDK2 kinase determined).

Analogs may also be developed by generating a library of molecules, selecting for those molecules which act as ligands for a specified target, and identifying and amplifying the selected ligands. See, e.g., Kohl et al., *Science*, 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 February 1994) and nonpeptide polymers (see, e.g., "peptoids" of Simon et al., *Proc. Natl. Acad. Sci. USA*, 89, 9367 (1992)). See also U.S. Pat. No. 5,270,170 to Schatz; Scott and Smith, *Science*, 249, 386–390 (1990); Devlin et al., *Science* 249, 404–406 (1990); Edgington, *BIO/Technology*, 11, 285 (1993). Peptide libraries may be synthesized on solid supports, or expressed on the surface of bacteriophage viruses (phage display libraries). Known screening methods may be used by those skilled in the art to screen combinatorial libraries to identify peptides which bind to CDC2 or otherwise act as Rak peptides. Techniques are known in the art for screening synthesized molecules to select those with the desired activity, and for labelling the members of the library so that selected active molecules may be identified. See, e.g., Brenner and Lerner, *Proc. Natl. Acad. Sci. USA*, 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA*, 89, 9367, (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target, such as cdc2. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for proteins. See, e.g., Edgington, *BIO/Technology*, 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA*, 89, 8864 (1992) and Tsai and Keene, *J. Immunology*, 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

B. Proteins and Peptides

The proteins and peptides of the invention may be made in accordance with techniques known in the art. Using accepted techniques of chemical synthesis, the peptide is built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide.

Peptides and fusion proteins of the present invention may also be produced through recombinant DNA procedures. Nucleotide sequences for DNA sequences which code for peptides or fusion proteins of the present invention (useful as intermediates for making the same) can be determined with any table setting forth the genetic code. See, e.g., R. Old and S. Primrose, Principles of Gene Manipulation, 346 (3d ed. 1985).

The production of recombinant DNA, vectors, host cells, and proteins by genetic engineering techniques is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicants specifically intend that the disclosures of all U.S. Patent references cited herein be incorporated by reference herein in their entirety).

DNA sequences encoding desired proteins may be recovered by use of the polymerase chain reaction (PCR) procedure and splicing by overlap extension (SOE), as is known in the art. See U.S. Pat. No. 4,683,195 to Mullis et al. and U.S. Pat. No. 4,683,202 to Mullis.

The proteins may be synthesized in host cells transformed with vectors containing DNA encoding the proteins. A vector is a replicable DNA construct. Vectors are used herein either to amplify DNA encoding the protein and/or to express DNA which encodes the protein. An expression vector is a replicable DNA construct in which a DNA sequence encoding the protein is operably linked to suitable control sequences capable of effecting the expression of the protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the protein vectors constructed using recombinant DNA techniques. Transformed host cells ordinarily express the protein, but host cells transformed for purposes of cloning or amplifying the protein DNA need not express the protein.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and *Serratia marcesans* are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trpl gene, which provides a selection marker for a mutant strain of yeast lacking the ability to grow in tryptophan, for example ATCC No. 44076 or PEP4-1 (Jones, *Genetics* 85, 12 (1977)). The presence of the trpl lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g.

Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

C. Administration and Subjects

The peptides, fusion proteins and other molecules of the present invention may be prepared per se or in the form of pharmaceutically acceptable salts thereof. Pharmaceutically acceptable salts are those that retain the desired biological activity of the parent compound and do not impart undesired toxicological effects. For example, acid addition salts of acetate, adipate, alginate, aspartate, benzoate, benzenesulfonate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrochloride, hydrobromide, hydroiodide, 2-hydro-xyethanesulfonate, lactate, maleate, methanesulfonate, 2-naphthalenesulfonate, nicotinate, oxalate, pamoate, pectinate, persulfate, 3-phenylproprionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Molecules of the present invention may also be formulated to increase membrane permeability, such as by using lipid vesicle delivery systems, or by the incorporation of hydrophobic cleavable protective groups, as is known in the art.

Pharmaceutical formulations of the instant invention comprise the desired molecules in a pharmaceutically acceptable carrier, such as sterile, pyrogen-free water or sterile pyrogen-free phosphate-buffered saline solution. The molecules described above being the active ingredient in these compositions, they should be included in an amount effective to accomplish the intended treatment. The precise amount to be administered to a subject is determined in a routine manner, and will vary depending on the subject, condition being treated, severity of the condition, and route of administration. The effectiveness of a dosing regimen may be ascertained by measures known in the art, including but not limited to in vitro assays, amelioration of clinical symptoms or laboratory signs, or a decrease in the rate of cell growth. When used as a treatment for cancer or other neoplastic disease, or as an anti-proliferative treatment for non-cancerous conditions, the molecules of the present invention may be used in conjunction with other treatments.

For the preparation of these compositions, use can be made of pharmaceutical carriers adapted for all conventional forms of administration, for example, tablets, capsules, dragees, syrups, solutions, suspensions, aerosols and the like. As injection medium, it is preferred to use water which contains the additives usual in the case of injection solutions, such as stabilizing agents and/or buffers.

Any suitable route of administration may be employed in carrying out the methods of the present invention, including but not limited to oral administration, intranasal or inhalation administration, intravenous injection, intraarterial injection, intraperitoneal injection, intramuscular injection, and subcutaneous injection.

Subjects to be treated by the methods disclosed herein are preferably mammalian subjects, such as human, cat, dog, rodent and horse subjects. Thus the present invention has both medical and veterinary applications.

The following examples are provided to illustrate the present invention, and should not be construed as limiting thereof.

EXAMPLE 1

Materials and Methods

Cell Lines, Tumors, and Antibodies. Human tumor cell lines were obtained from the American Type Culture Collection, except for the RD cell line, which was the kind gift of Dr. Bernard Weissman. Primary human tumors were obtained from operative specimens at University of North Carolina Hospitals via Institutional Review Board-approved protocols. Antibodies to Src and Fos were obtained from Oncogene Science (Uniondale, N.Y.), and antibodies to the human FGFR-4 were purchased from UBI (Lake Placid, N.Y.).

Isolation of cDNA Clones. A cDNA library from the breast cancer cell line BT20 was prepared using 5 $\mu$g of poly(A)$^+$ RNA as a template for reverse transcriptase. The cDNA was ligated to $\lambda$gt10 digested with EcoRL and then packaged into phage heads with the Giga Pack Gold packaging extract (Stratagene, La Jolla, Calif.) and plated with *Escherichia coli* C600 cells. Libraries were screened with a 210-bp fragment of rak isolated previously (Cance et al., *J. Cancer* 54:571–577 (1993)), which was labeled with [$\alpha$-$^{32}$P] dCTP by incorporation during PCR (Jansen R. and Ledley F D, Production of discreet high specific activity DNA probes using the polymerase chain reaction *Gene Anal. Tech.,* (1989)). Production of discreet high specific activity DNA probes using the polymerase chain reaction. Positive clones were isolated, and the insert was subcloned into the Not1 site of pKS BlueScript (Stratagene), then sequenced with the dideoxy chain-termination method. Sequences were analyzed using the FASTA program from the University of Wisconsin Genetics Computer Group.

Northern Blotting. The human Multiple Tissue Northern Blot I (Clontech, Palo Alto, Calif.) was probed with a 2200-op pvull fragment of the rak cDNA clone. The probe was prepared by eluting the fragment from an agarose gel, and the DNA was labeled by the random priming technique using the Genius system (Boehringer Mannheim, Indianapolis, Ind.) then purified by chromatography on a Sepharose G-50 column in 20 mM Tris (pH 8.0) with 0.1 mM EDTA. The probe from β-actin was prepared by adding [α-$^{32}$P]dCTP to a PCR reaction containing the following primers: actin 5',5'-CCTTCCTGGGCATGGAGTCCTG-3' (SEQ ID NO:5); and actin 3',GGACAATGATCTTGATCTTC-3'(SEQ ID NO:6). The probe was purified over a Sepharose G-50 column.

The Northern blot was incubated in hybridization buffer (50% formamide, 5×sodium, 5×Denhardt's, 0.1% SDS, 5 mM Na$_2$HPO$_4$, and 100 μg/ml denatured salmon sperm DNA) at 42° C. overnight, and then the probe was boiled and added to hybridization buffer to a concentration of 5×10$^6$ cpm/ml, then incubated at 42° C. overnight. The blot was washed to a final stringency of 0.5×standard saline-citrate/ 0.1% SDS at 56° C. for 45 min and then exposed to film at −70° C.

Recombinant Peptide and Antibody Preparation. For the preparation of antibodies, a 1600-bp HindIII fragment comprising the 3'-end of the rak gene was subcloned into the HindIII site of the pQe30 plasmid (Qiagen, Chatsworth, Calif.), forming a fusion protein of six histidine residues and amino acids 288–505 of the Rak protein, and this peptide was name the HindIII antigen. Induction and lysis of E.coli cells were performed according to the manufacturer's specifications, except that 10 mM imidazole was included in the binding of the peptide to the Ni$^{2-}$ bound column and subsequent washes. In order to "renature" the peptide, a step gradient of 7–0 M urea was performed in renaturation buffer (50 mM sodium bicarbonate (pH 8.5), 500 mM NaCl, and 20% glycerol), followed by an extensive wash with renaturation buffer. The protein was eluted in renaturation buffer containing 100 mM imidazole. The carboxy-terminal 62 amino acids were produced as a hexahistidine fusion protein by incorporating restriction enzyme sites in the ends of PCR primers and cloning the resultant PCR fragment into the BamH1 and HindIII sites of the pQF3U plasmid (Qiagen). The primer sequences were 5'-CGGATCCCAGATGTTCGCTC-3' (SEQ ID NO:7) and 5'GAAGCTTAGTAGAATACTTCAA-3' (SEQ ID NO:8). The identity of the clone was confirmed by sequencing, and the fusion protein was referred to as the QAg (the coding sequence begins QMLAQ). Following purification, the recombinant peptides were emulsified in complete Freund's adjuvant and used for antibody preparation in New Zealand White rabbits. Subsequent boosts were performed in complete Freund's adjuvant according to standard protocols (See Harlow and Lane, Antibodies: A Laboratory Manual, Cold Spring Harbor, N.Y.; Cold Spring Harbor Laboratory (1988)). The antibody to the HindIII antigen was referred to as VH55, and the antibody to the QAg as VQ41.

In vitro transcription/translation was performed using the Tnt-coupled transcription/translation system (Promega, Madison, Wis.). Two μg of plasmid were added to the reactions, and the plasmids used were prak-2 for Rak and 8A3-cs ior Sil (the kind gift from Dr. Don Fujita, University of British Columbia, Vancouver). Reactions were resolved on SDS-PAGE or immunoprecipitated using the protocol outlined in the following section.

Western Blots and Immunoprecipitations. For the preparation of whole-cell lysates, cells were washed once with cold PBS, then overlayed with NP-40 lysis buffer (1% NP-40, 20 mM Tris (pH 7.4), 150 mM NaCl.5 mM EDTA, 1 mM Na$_3$VO$_4$ and 10 μg/ml of the protease inhibitors aprotinin and leupeptiol on ice for 10 min and then harvested. The samples were cleared by centrifugation at 12,000 rpm for 10 min at 4° C., and the protein concentration was measured with the BCA assay (Pierce, Rockville, Ill.). Tumors were extracted in the same buffer but were disrupted with a Polytron P11200 for 20 s on the maximum setting. Western blotting was performed according to established methods (See Harlow and Lane, Antibodies: A Laboratory Manual, Cold Spring Harbor, N.Y.; Cold Spring Harbor Laboratory (1988)), with 30 μg of protein loaded in each lane. The multiple tissue Western blot was purchased from Clontech and contained 75 μg of protein per lane. The VH55 antibody was used for Western blotting at 1:1000 dilution.

For immunoprecipitation, 250 μg of protein was incubated with 10% protein A-Sepharose (Pharmacia, Piscataway, N.J.). Ten μl of the VQ41 antiserum was used for in vitro kinase assays, as it is not directed to the kinase domain. The reactions were brought to 500 μl with NP-4U lysis buffered and incubated at 4° C. for 2 h. Following incubation, the pellets were washed three times with NP-40 lysis buffer. For kinase assays, the pellets were washed twice with 10 mM HEPES (pH 7.4) and 5 mM MnCl$_2$ and then were resuspended in 40 μl of the same. The reaction was initiated with the addition of 10 μCl of [γ-$^{32}$P] ATP (3000 Ci/mmol; NEN) and incubated at 30° C. for 15 min; then the reaction was terminated with the addition of SDS-PAGE sample buffer. The samples were boiled and analyzed on a 10% SDS-PAGE gel, then dried and exposed to film.

Peptide, Preparation for Phosphorylation. Initially, the OAg was tested for phosphorylation by CSK in an in vitro kinase reaction and was phosphorylated. To further assess which tyrosine was phosphorylated, each of the four tyrosines in the substrate peptide were mutated to phenylalanine by the double-stranded, site-directed mutagenesis method (Deng and Nickoloff. Site-directed mutagenesis of virtually any plasmid by eliminating a unique site. *Anal. Biochem.*, 200:81–88 (1992)). The plasmid was denatured by heating to 100° C. for 5 min and then annealed to a mutagenic primer and a second primer converting an Af/AII site on the plasmid to a Bg/II site. The mutagenic primers for the four tyrosines were: Y45Uf, 5'-GCTCAAAACTTTAGACTTCC-3' (SEQ ID NO:9); Y163F, 5'-ACAGCAATTTTTCAACATCA-3' (SEQ ID NO:10); Y490F, 5'-TGAAGAC-TTTTTTGAAACAG-3' (SEQ ID NO:11); and Y497F, 5'-ACTCTTCATTTTCAGATGCA-3' (SEQ ID NO:12).

The primers were extended with 3 units DNA polymerase (New England Biolabs, Beverly, Mass.), ligated with 4 units T4 DNA ligase (New England Biolabs), and transformed into *E. coli* BMH71-18 mutS cells. Plasmids from the pool of transformants were then prepared, digested with Af/III, and used to transform *E. coli* [M]09 cells. The resulting colonies were then screened for mutations by sequencing.

Purified μ50$^{csk}$ and Enzyme Assays. p$_{50}$$^{csk}$ was produced in S/9 cells from a Baculovirus vector containing the full-length csk cDNA (Okada et al., *J. Biol. Chem;* 264:20886–20893(1989)), purified according to Murphy et al. (*Mol. Cell. Biol.*, 13:5290–5300 (1993), and mixed with the different peptides of Rak. These peptides correspond to the last 62 amino acids of the kinase, containing four tyrosine residues (Y450, Y463, Y490, and Y197), and mutant peptides where each of the four tyrosines was deleted. The phosphorylation of the native peptide was compared to the that of the mutant peptides. For the in vitro kinase assay, different amounts of p50$^{csk}$ were mixed with different amount of the peptides in a reaction buffer (10 mM HEPES (pH 7.4) 10 mM MnCl$_2$1. Four μg bovine serum albumin were added to the 20-μl mixture, and the reaction was initiated with the addition of AIP to 1 μm and 10 μCl of 1 γ-$^{32}$P)ATP (3000 Ci/mmol; Amersham). Tubes were incubated at 30° C. for 15 min, and the reaction was stopped by the addition of SDS-PAGE sample buffer. The samples were boiled and analyzed on 15% SDS-PAGE gels, which were fixed, stained, and exposed to film at 70° C.

Immunofluorescence and Subcellular Fractionation. COS7 cells (1×10$^5$) were plated on 4-well chamber slides and fixed with 3.7% formaldehyde in PBS; then they were permeabilized with PBS containing 0.1% Triton X-100. The slides were blocked with 10% normal goat serum, incubated with antibodies to Rak at a 1:200 dilution in PBS containing 2% bovine serum albumin, and washed three times with PBS. For detection, the slides were incubated with fluorescein isothiocyanate-conjugated goat anti-rabbit secondary antibodies in PBS with 2% normal goat serum and then examined with a fluorescence microscope.

For subcellular fractionation, COS-7 cells were washed once in PBS and harvested with a cell scraper; then they were lysed by resuspension in the buffer (10 mM HEPES (pH 7.4), 60 mM KCl, 1 mM EDTA, 1 mM dithiothreitol, 1 mM phenylmethylsulfonyl fluoride, 1 mM Na$_3$VO$_4$, 10 μg/ml each aprotinin and leupeptin, and 0.15% Triton X 1001. The cells were left on ice for 5 min; then they were centrifuged at 1000×g for 4 min. The supernatant was collected and contained cytoplasmic and membrane proteins. The pelleted nuclei were then washed once in CE buffer that did not contain Triton X-100, centrifuged, and lysed by resuspension in the same 1% NP-40 lysis buffer used for Immunoprecipitations; then they were mixed at 4° C. for 15 min. The preparation was then clarified by centrifugation at 10,000×g for 20 min.

EXAMPLE 2 cDNA Cloning and Sequence Analysis of the Novel Tyrosine Kinase, Rak

A 210 bp fragment of rak was originally isolated using degenerate PCR primers directed to consensus sequences in the kinase domain. (Cance et al., *J. Cancer* 54:571–577 (1993)). This fragment was used to probe a cDNA library from the BT-20 breast cancer cell line and a 2827 bp (SEQ ID NO:1) full-length clone for rak was obtained (FIG. 1). Sequence analysis of this clone predicted a protein of 505 amino acids. The closest homologue to rak was a Hydra attenuata kinase, STK (for src-type kinase; see Busch et al., *Mol. Cell Biol.* 9:4141–4151 (1989)), which shared a 54% identity. Among the human tyrosine kinases, Rak was most similar to Lyn and Src, both of which shared approximately a 50% identity. Since the src family of kinases generally share approximately a 70% identity, Rak appeared to be a distant member of this group of kinases.

Comparison of the amino acid sequence of Rak with other Src family members revealed several similarities. The protein encoded by Rak contained a putative Mg$^{+2}$-ATP binding site at amino acids 241 to 264 with the consensus sequence GxGxxG . . . AxKxL, as well as the SH3 and SH2 domains, which are postulated to play a role in protein-protein interactions as well as regulation of kinase activity. In addition, Rak contained a putative autophosphorylation site at Y387, analogous to the Y416 of Src. The carboxy-terminal tyrosine of Rak was also positioned similarly to the Y527 of Src.

However, the amino acid sequence of Rak had significant differences from other Src family members. The Src family members contain an amino terminal sequence, recently termed the SH4 domain (*Cell*, 76:411–413 (1994)), which directs binding to the cell membrane. This region of approximately 15 amino acids consists of a myristylation motif, MGxxxS/T, followed by a stretch of basic amino acids, and in the case of Lck and Fyn, a palmitylation motif, CxxC or CxC. In contrast, Rak did not contain either a myristylation or palmitylation motif but rather had a serine residue at position 2 and contained fewer basic amino acids within this region than Src family kinases. This suggested that Rak is an intracellular kinase which is not bound to the cell membrane. The Rak protein also has the sequence ESR immediately adjacent to the putative autophosphorylation site at Y387, in contrast to the TAR motif, which is most commonly seen in the other Src family members.

The Rak SH2 and SH3 domains differed from the Src family members. The Rak SH2 domain contained a putative bipartite nuclear localization signal extending from amino acids 168 to 181. This KRxxxxxFFxxRRR motif is not shared by other Src family members. By analogy to the structure of the Src SH2 domain (*Nature*, 358:646–653 (1992)), the two parts of this sequence would lie on the exposed end of the 4'strand and the strand 5 and 6 of the B β-sheet, thus increasing the likelihood that this sequence is accessible to other proteins. The Rak protein also contains other sequences in the SH2 and SH3 domains that are unlike the members of the Src family: a seven-amino acid insert between the C and D β-strands of the SH3 domain and a feature shared with Abl, a five-amino acid deletion between the SH2 domain strands 3 and 4 of the A β-sheet (FIG. 2) All of these sequences would be predicted to face the exterior of the molecule and would not be situated in the proposed binding pockets of the SH3 and SH2 domains.

EXAMPLE 3

The Rak Gene Encodes a M54,000 Protein with Autophosphorylation Activity

Using the 2.8-kb rak cDNA clone as a template for in vitro transcription and translation, we detected a M 54,000 protein (data not shown), which is the size predicted by the cDNA sequence. The same reaction performed on the host vector lacking the rak gene did not produce a translation product (data not shown). In order to study the biology of Rak, two sets of antibodies to the carboxy terminus of the Rak protein were generated. The VQ41 antibody was generated to the 62 carboxy-terminal amino acids and was used for in vitro kinase assays, since it was not generated to the catalytic domain, while the VH55 immunogen encompassed the 217 amino acids of the carboxy-terminal of Rak and was used for all of the other experiments. The VH55 antibody efficiently immunoprecipitated the M$_r$ 54,000 translation product (data not shown) and appeared to be specific for p54$^{rac}$, since no immunoreactivity was detected in preimmune serum (data not shown) or when the antibody was preincubated with the fusion protein immunogen (data not shown). Since the immunogenic peptide contained sequences that are common to Src, the Src protein was translated in vitro and it was found that the antibodies do not immunoprecipitate p60$^{src}$ and thus are not cross-reactive with p60$^{src}$ (data not shown).

Figure 3B:
FIG. 3B shows autophosphorylation activity of p54$^{rak}$ in the BT20 cell line, measured by immunoprecipitation followed by incubation with [$^{32}$P]ATP. The p54$^{rak}$ protein was immunoprecipitated with non immune serum (Lane 1) or antibody VQ41, generated to the carboxy-terminal 62 amino acids (Lane 2).
Figure 3C:
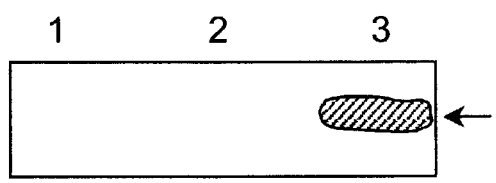
FIG. 3C is a Western blot of p54$^{rak}$ expression in normal colonic tissue, a primary colon carcinoma and a metastatic liver tumor from the same patient, detected with antibody VH55.

To assess whether p54$^{rak}$ encodes a functional kinase, p54$^{rak}$ was immunoprecipitated from the BT20 cell line using the anti-Rak antibody VQ41; an in vitro kinase assay was performed by incubating the immunoprecipitated protein with [$^{32}$P]ATP; p54$^{rak}$ demonstrated strong autophosphorylation activity (FIG. 3B, lane 2). The preimmune serum did not precipitate any appreciable autophosphorylation activity (FIG. 3B, lane 1), and the autophosphorylation activity was not detected when the antibody was preincubated with the immunogenic peptide (data not shown). In addition, p54$^{rak}$ translated in vitro was immunoprecipitated by antibodies to phosphotyrosine, suggesting that p54$^{rak}$ has intrinsic tyrosine kinase activity (data not shown).

EXAMPLE 4

The Expression of Rak in Human Tissues, Tumors and Cell Lines

Rak expression in seven human tumor cell lines and nine breast tumors has been studied using reverse transcription-PCR (Cance et al., *J. Cancer* 54:571–577 (1993)). This indicated that rak was expressed primarily in breast cancer cell lines and was differentially expressed in the series of breast tumors. This study was expanded using Northern blot analysis of a panel of normal human tissues. It was found that rak was expressed at the highest levels in tissues of epithelial origin. The rak mRNA was a 3-kb transcript which was highly expressed in epithelial tissues, such as kidney, liver, and lung, but barely detectable in the mesenchymally derived skeletal muscle. A second transcript of approximately 10.5 kb was also detected in all tissues except lung (data not shown). These same tissues were examined at the protein level using Western blot analysis and again found that rak was expressed predominantly in epithelial tissues, with liver and kidney containing the highest levels of p54$^{rak}$. Thus, the expression patterns of the $M_r$54,000 Rak protein correlated with the expression of the 3-kb rak transcript in all tissues except lung (data not shown). The 3-kb transcript appears to encode the p54$^{rak}$.

As rak had originally been isolated from a human breast cancer cell line, the levels of expression of p54$^{rak}$ in a panel of human tumor cell lines and primary tumors was examined. In 13 cell lines of epithelial, mesenchymal, and hematopoetic origin, the highest levels of expression of p54$^{rak}$ were detected in epithelial cell lines (FIG. 3A), most prominently in the BT-20 breast cancer cell line and the LS180 colon cancer cell line. There were low but detectable levels of p54$^{rak}$ in the hematopoetic cell lines K562 and HL60.

Figure 3D:
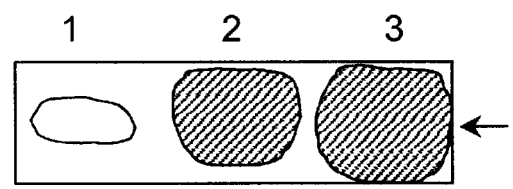
FIG. 3D shows p54$^{rak}$ autophosphorylation activity in human tumors. In vitro kinase assay on the primary colon cancer (from Lane 2 of FIG. 3C) immunoprecipitated with preimmune serum (Lane 1) or anti-Rak antibody VQ41 (Lane 2), demonstrated low levels of p54$^{rak}$ autophosphorylation, although expression of p54$^{rak}$ was not detected by Western blotting, above. Lane 3 rrepresents the same assay of the metastatic colon cancer sample (from Lane 3 of FIG. 3c) with the VQ41 antibody, demonstrating high levels of activity consistent with the Western blot results.

In primary human tumors, expression of RAk predominantly in cells of epithelial origin was confirmed. In subsets of human breast and colon tumors, overexpression of p54$^{rak}$ was found in approximately 30% of tumors analyzed. Using Western analysis, increased levels of p54$^{rak}$ in two of five colon cancers and two of six breast cancer were found, compared to their normal tissue counterparts (data not shown). Also examined was p54$^{rak}$ activity in these samples by immunoprecipitating p54$^{rak}$ in high stringency buffer and assessing intrinsic autophosphorylation activity. It was found that p54$^{rak}$ autophosphorylation activity paralleled the increase in expression in these samples (FIG. 3D).

EXAMPLE 5

The Carboxy Terminus of Rak Is Phosphorylated by CSK. Since CSK phosphorylates the carboxy terminal tyrosines of several other Src-related kinases, the ability of CSK to phosphorylate a recombinant carboxy-terminal peptide of Rak was analyzed. A hexahistidine fusion protein was designed which contained the 62 carboxy-terminal amino acids of Rak but did not encompass the major consensus sequences found within the kinase domain. This peptide was readily phosphorylated by CSK (FIG. 8). Since this peptide contained four tyrosines at positions 450, 463, 490, and 497, each tyrosine was individually mutated to phenylalanine and then the peptides were assayed for phosphorylation by CSK. The mutant at position 463 was phosphorylated at levels equivalent to the wild-type peptide, and the mutants at positions 450 and 490 were phosphorylated to about one-half the extent of the wild-type peptide (FIG. 8). Phosphorylation of the 497 mutant, however, was barely detectable, suggesting that Y497 is the phosphorylation site for CSK. Indeed, this residue corresponds to the CSK phosphorylation site for the other Src family members with regard to its localization in regard to the kinase domain, although the sequence context of this tyrosine differs from that of the other Src-like kinases.

EXAMPLE 6

Nuclear Localization of p54$^{rak}$

Because of the putative nuclear localization signal in the Rak SH2 domain, as well as the lack of an amino-terminal myristylation site, the subcellular localization of p54$^{rak}$ was examined. Kidney cells were selected because they expressed the highest levels of p54$^{rak}$, and COS7 monkey kidney cells were chosen since they contained high levels of expression of p54$^{rak}$ as shown by Western analysis (FIG. 9A). By immunofluorescent staining, we found a predominance of immunoreactivity in the nuclei of the cells (FIG. 9B), as expected. The majority of the COS-7 cells expressed elevated levels of p54$^{rak}$ in their nuclei, while a smaller subpopulation of cells contained p54$^{rak}$ immunoreactivity in areas on the periphery of the cell as well as the nucleus.

To confirm these immunofluorescence results, the COS-7 cells were fractionated into their cytoplasmic/cell membrane and nuclear components. By Western analysis, p54$^{rak}$ located exclusively in the nuclear fraction (FIG. 9C). Furthermore, since the fractionation techniques may not yield completely pure nuclear and cytoplasmic/membrane preparations, the nuclear fraction was probed for the c-Fos protein and it was found that this exclusively nuclear protein cofractionated with p54$^{rak}$ (FIG. 9C). In contrast, the FGR-4 protein, a cell membrane-bound receptor, fractionated in the cytoplasmic and cell membrane portion (FIG. 9C), as did the c-Src protein (data not shown). In the BT-20 breast cancer cell line, which expressed p54$^{rak}$ at lower levels than COS7 cells, the protein was not contained exclusively in the nucleus but also was detected in the cytoplasm, suggesting that p54$^{rak}$ localization may vary in different cellular contexts (data not shown).

EXAMPLE 7

Because of the potential Rb binding site in the Rak amino-terminal region, the ability of Rak to associate with the tumor suppressor protein pRb was assessed. It was found that Rak associates with pRb by affinity precipitation of pRb with a Rak-GST fusion protein, from a cell lysate of the breast cancer cell line SK-BR-3. This finding was confirmed by immunoprecipitation of Rak and probing western blots for pRb. The interaction between Rak and Rb occurs primarily between the A/B pocket region of pRb and sequences within the Rak SH3 domain (amino acids 47–108 of SEQ ID NO:2), and results in an active tyrosine kinase co-precipitating with pRb. Biologically, Rak associates with pRb in the G1 and S phases of the cell cycle, and has elevated expression in G1 and S in comparison with mitosis. Transfection of Rak into 3T3 cells results in a significant reduction of G418-resistant colonies. Thus Rak is a growth suppressing tyrosine kinase that functions in part through its interaction with Rb.

The tumor suppressor pRb is a modular protein, which associates with a variety of proteins, including transcription factors and cyclins, through a 400 amino acid region of pRb termed the "A/B pocket". This region is thought to sequester and inactivate these proteins, and mutations in this region have been found in human tumors. At the C-terminus, pRb contains a "C pocket" which binds to the kinase domain of c-Abl, and together, the A, B and C pockets of pRb are believed to assemble complexes of proteins which are essential for growth arrest by pRb.

Rak was found to associate with the pRb "A/B pocket" in breast cancer cells in G1 phase cells, and it was found that Rak is active when bound, and that overexpression of Rak causes a reduction in cell growth.

Cell Cultures and Antibodies. BT474 and SK-BR-3 human breast cancer cells, and SAOS-2 human osteosarcoma cells were obtained from the ATCC, and were maintained according to their specifications. Preparation of protein lysates and immunoprecipitations were performed in NP-40 Lysis Buffer (50 mM Tris, 7.4, 1% NP-40, 150 mM NaCl, 1 mM EDTA, 1 mM $Na_3VO_4$, and 10 ug/ml of the protease inhibitors aprotinin and leupeptin). For immunoprecipitations, 1 ug of the anti-Rb monoclonal antibody G3-245 or 15 ul of the anti-Rak antibody RH55 was used. Rak immunoprecipitation reactions were blocked with the addition of approximately a 10-fold excess of immunogenic fusion protein. For in vitro kinase assays, Rb was immunoprecipitated, then washed with Kinase Buffer (10 mM HEPES, pH 7.4, 5 mM $MnCl_2$, and 1 mM dithiothreitol) twice, then resuspended in 30 ul Kinase Buffer. To initiate the kinase reaction, 10 uCi of [32P]-ATP was added, and the reaction was incubated at 30° C. for 15 minutes, then stopped with SDS-PAGE sample loading buffer and analyzed by SDS-PAGE. Following electrophoresis, the gels were fixed, then soaked in 1 M KOH at 55° C. for 1 hour, then fixed again, dried, and autoradiographed. Cells were synchronized in the G1, S, and M phases of the cell cycle by serum starvation, 1 mM hydroxyurea (Sigma) and 40 ng/ml nocodazole (Sigma). Antibodies to cyclin A and CDC2 were purchased from Santa Cruz.

Affinity Precipitations. DNA fragments encoding the amino terminal region of Rak were prepared using the polymerase chain reaction with *Pyrococcus furiosus* DNA polymerase (Stratagene), and cloned into the pGEX-4T plasmid (Pharmacia). Rb fusion proteins encoding amino acids 379–928 (RbABC, containing the A/B pocket region and the COOH-terminal domain) and 780–928 (RbC for COOH terminal domain only), were prepared similarly. The GST fusion proteins were induced and purified according to the manufacturer's instructions, and were analyzed by SDS-PAGE to ensure that an equal amount of protein was used for the affinity precipitation procedure.

For affinity precipitations, 250 ug of cell lysate was pre-cleared once with 25 ul of glutathione-sepharose beads (Pharmacia) then once with 25 ul of the same beads containing 2 ug/ml Glutathione S-transferase. The lysate was then incubated with 25 ul of GST-RakNT bound to glutathione-sepharose, in a total volume of 500 ul of NP-40 lysis buffer, for 3 hours at 4° C. The beads were then washed three times in NP-40 Lysis Buffer and the bound proteins were eluted with SDS-PAGE sample loading buffer. pRb binding was assessed by Western blot analysis with the G3-245 antibody at 1 ug/ml.

The same procedure was followed for Rb in vitro binding assays, except that the Rb-GST fusion proteins were incubated in the in vitro translated forms of Rak in NP-40 buffer containing 0.5% fraction V bovine serum albumin (Boehringer Mannheim). After three washes with the same buffer, bound proteins were analyzed by SDS-PAGE and detected by autoradiography. Rak was in vitro translated using the TnT-coupled transcription/translation system (Promega) with 2 ug of the pAlt-Rak plasmid. The Rak (1–152) construct was prepared by digesting the pAlt-Rak plasmid with EcoRI to obtain the 5' EcoRI fragment of Rak.

Figure 4A:
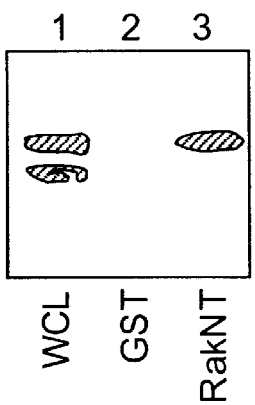
FIG. 4A is a Western blot of an affinity precipitation reaction using the Rak amino terminal fusion protein. An SK-BR-3 lysate (lane 1) was incubgated with GST alone (lane 2) or GST-RakNT (lane 3), and bound proteins were analyzed by Western blot analysis for pRb.

Results and Discussion: To test whether Rak and pRb physically interact, the first 110 amino acids of Rak (first 110 amino acids of SEQ ID NO:2), where the predicted interacting peptides reside were prepared as a bacterial fusion protein with the Glutathione-S transferase gene (Rak-NT:GST), and incubated with cell lysates from SK-BR-3 breast cancer cells, and bound proteins were analyzed by Western blotting. Glutathione-S transferase alone was used as the control. By this assay, it was found that pRb bound to this Rak amino terminal fusion protein (FIG. 4A, lane 3). In contrast, binding of Rak to proteins that interact with the SH3 domains of other members of the Src family, such as GAP-associated p62 or Shc, was not found (data not shown).

Figure 4B:
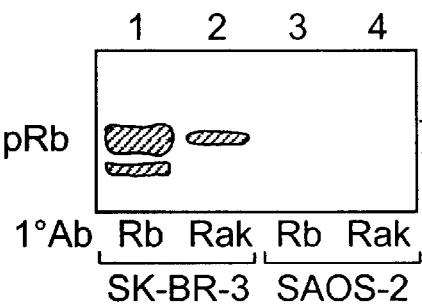
FIG. 4B shows the in vivo association of Rak with pRb. pRb (lanes 1 and 3) or Rak (lanes 2 and 4) were immunoprecipitated from SK-BR-3 (Rb+) or SAOS-2 (Rb−) cells, and pRb was detected by Western blot.
Figure 4C:
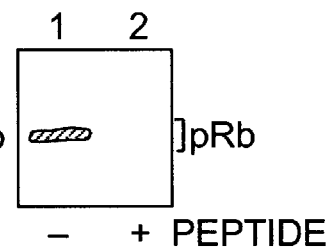
FIG. 4C shows that Rak was immunoprecipitated in the absence (lane 1), or the presence (lane 2) of immunogenic peptide, and analyzed by Western blot for pRb.

To assess whether the interaction between Rak and pRb occurs in vivo, Rak was immunoprecipitated from two cell lines, SK-BR-3 and SAOS-2, in which only the former expresses the Rb protein, and the precipitates were immobilized with antibodies to pRb. These data revealed that pRb co-precipitated with Rak in SK-BR-3 cells, whereas no bands representing pRb bound to Rak were present in immunoprecipitation reactions from SAOS-2 cells (FIG. 4*b*). As a control, the immunogenic peptide for the anti-Rak antibody was added as a competitor which effectively blocked the co-precipitation of Rb with Rak in SK-BR-3 lysates.

Figure 5A:
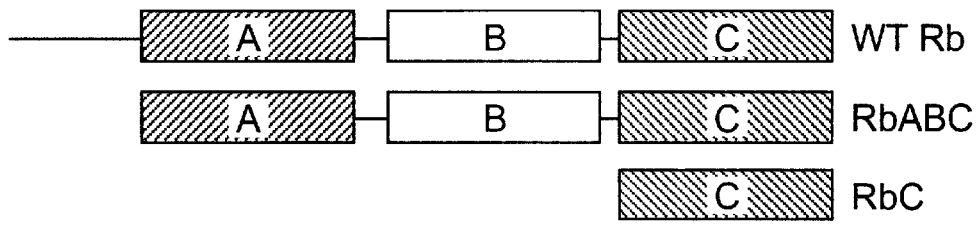
FIG. 5A is a diagram of the pRb fusion proteins used in the binding reacitons.
Figure 5B:
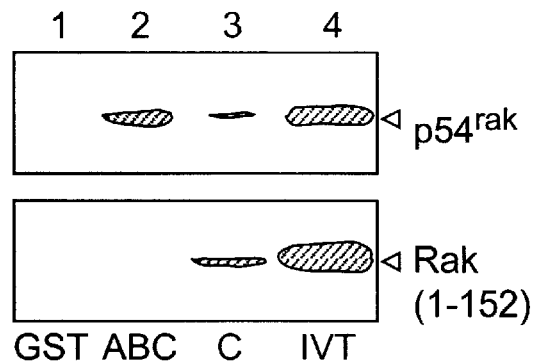
FIG. 5B: In vitro translated Rak (upper panel, lane 4) or the amino-terminal 152 amino acids of Rak (lower panel, lane 4) were incubated with GST alone (lane 1), GST-RbABC (lane 2), or GST-RbC (lane 3), and bound proteins were analyzed by SDS-PAGE and autoradiography.
Figure 6:
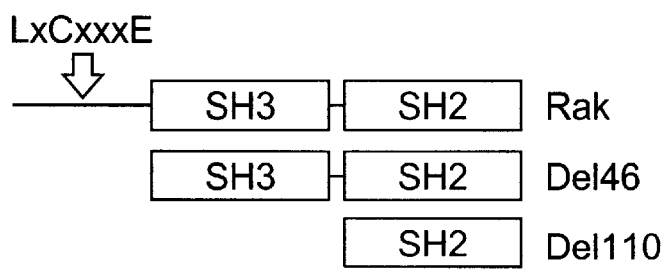
FIG. 6 is a diagram of Rak fusion proteins used in binding reactions to assess the Rak-Rb interaction. Rak contains the unique N-terminal binding region and the SH2 and SH3 domains. Deletion of amino acids 1–46 (SEQ ID NO:13) of Rak removed the unique N-terminal region; deletion of amino acids 1–110 removed the unique N-terminal region and the SH3 domain.

An in vitro binding reaction was then used to further identify the essential components for the Rak-Rb interaction. In vitro translated Rak was incubated with two Rb-GST fusion proteins, where one encoded amino acids 379–928, spanning the A/B pocket and carboxy-terminus (RbABC), while the other fusion protein encoded amino acids 780–928, and represented only the carboxy-terminus (RbC). The in vitro translated full-length Rak protein bound efficiently to the RbABC fusion protein, and approximately 5-fold less to the RbC protein (FIG. 5B, upper panel). However, an amino-terminal fragment of Rak which included the unique amino-terminal region and the SH3 domain (amino acids 1–152), bound with approximately 30% less efficiency overall to the RbABC fusion protein, and binding to the RbC protein was no longer detectable (FIG. 5B, lower panel). To determine which sequences of Rak are required for the Rak-Rb association, amino acids 1–46 (SEQ ID NO:13) of Rak were deleted (FIG. 6), removing the LPCLSTE sequence which resulted in no change in Rb binding. In contrast, deletion of amino acids 1–110 in Rak (FIG. 6), which removes the unique N-terminal region and the SH3 domain, resulted in Rb-Rak interaction that was minimally detectable (data not shown). As a control, the Src protein was in vitro translated and subjected to the same binding reaction, and no binding of Src to any portion of Rb was detected (data not shown).

These results suggest that in binding between Rak and Rb, the SH3 domain of Rak binds to sequences within the A/B pocket region of Rb, and with a lesser interaction between C-terminal sequences of Rak and the Rb C pocket. Binding of Src-related kinases to proteins via their amino-terminal region frequently activates the kinases, presumably by making key regulatory tyrosine residues accessible to tyrosine kinases and/or phosphatases. Rak may thus be active when bound at its amino terminus to pRb; indeed it was found that pRb precipitates with a 54 kDa protein with tyrosine kinase activity and this p54 kinase did not co-precipitate in cell lines which express Rak but no pRb, or express pRb but not Rak, or express pRb but not Rak.

Breast cancer cells were synchronized in G1, S and M phases of the cell cycle using serum starvation and chemical treatment (Levedakou E et al., *Oncogene*, 9:1977–1988 (1994). Rak was found to associate with pRb in G1 and late G1. Rb was hyperphosphorylated in S and M phase cells, and cyclin A reached peak expression in S phase. Rak was most highly expressed in G1 phase, following 48 hours of serum starvation, and was expressed to a lesser degree during mitosis. Furthermore, Rak co-precipitated with pRb not only in G1 but also in S phase, but not in cells arrested in G2/M. Therefor, Rak binds to Rb at specific times in the cell cycle.

Because Rak is an active kinase when bound to pRb, has elevated expression in arrested cells, and binds to pRb in G1 and S phases, constitutive overexpression of Rak should be inhibitory to cell growth. To test this, Rak was transfected in NIH 3T3 cells using pcDNA3 (vector alone), pc3-Rak (vector containing rak), or pc3-Rak(delKD) (vector containing rak in which the kinase domain was deleted). Three days following transfection, the cells were plated at $1 \times 10^6$ cells/plate and grown in neomycin selection for 3 weeks. Colonies were then stained and counted. The results from three separate trials are shown in TABLE 1. Cells transfected with Rak exhibited a 60% decrease in growth compared with cells transfected with vector alone.

Thus Rak was not transforming but rather caused a reduction in the number of viable 3T3 colonies following transfection. This inhibitory activity maps to the N-terminal 130 amino acids of Rak, which includes a unique N-terminal region and the SH3 domain.

TABLE 1

Growth Reduction Assay
(Number of colonies counter per trial)

|  | I | II | III | avg. |
|---|---|---|---|---|
| pcDNA3 | 131 | 173 | 112 | 100% |
| pc3-Rak | 51 | 81 | 48 | 43% |

EXAMPLE 8

Deletion analysis revealed that binding of CDC2 required amino acids 87–110 (SEQ ID NO:3), which are within the rak SH3 domain. To explore these interactions in vivo, $p54^{rak}$ was immunoprecipitated from BT474 cells, and in vitro kinase assays revealed that rak was part of a complex containing Rb phosphorylating activity. Like the Rb phosphorylating activity of CDK4, this activity was sensitive to lysis in Triton X-100, while rak autophosphorylation activity was not.

Because the N-terminus is frequently responsible for protein-protein interactions in Src-related kinases, the proteins that bind to this region were characterized. The N-terminal 110 amino acids of Rak were expressed as a bacterial fusion protein with Glutathione S-transferase, and were incubated with cell lysates from BT474 breast cancer cells. In this assay, binding of RAK to the cyclin-dependent kinases Cdc2 and Cdk4 was detected, but binding to Cdk5, Cdk6, or Cdk7 was not detected (data not shown).

Figure 7:
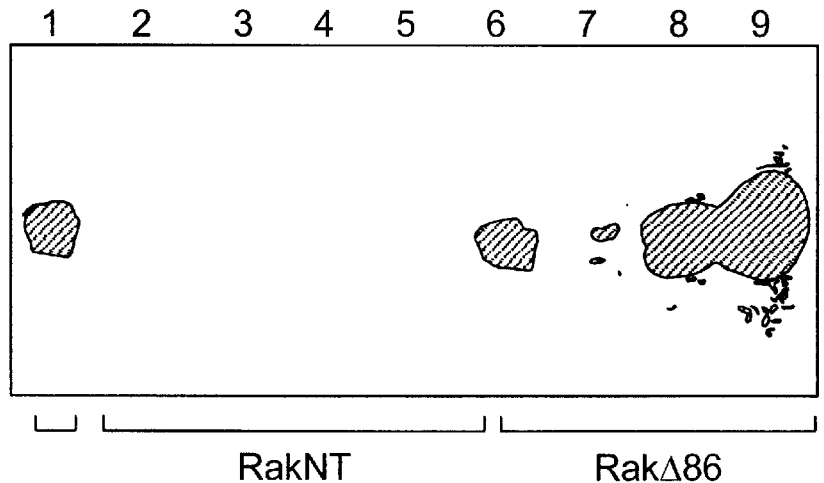
FIG. 7 shows the reduction of CDC2 histone H1 phosphorylation activity with the RakNT fusion protein. The 110 N-terminal amino acids of Rak were used to produce a RAK:GST fusion protein which was incubated with immunoprecipitated CDC2, subjected to an in vitro kinase assay with Histone H1 added as an exogenous substrate, and analyzed by SDS-PAGE. Lanes 2–5 depict a 1:2 serial dilution of the RakNT fusion protein; lanes 6–9 depict a Rak fusion protein in which amino acids 86–110 were deleted.

By deletion analysis, the site of the Rak-Cdc2 interaction was mapped to the C-terminus of the Rak SH3 domain, while this deletion did not affect binding of Rak to Cdk4. The 110 N-terminal amino acids of Rak were produced as a GST fusion protein (RAKNT:GST) and incubated with immunoprecipitated CDC2, and subjected to an in vitro kinase assay with Histone H1 added as an exogenous substrate, and analyzed by SDS-PAGE. A 1:2 serial dilution of the RakNT fusion protein is shown in FIG. 7, lanes 2–5. To demonstrate the importance of amino acids 86–110 of Rak, this sequence was deleted from the same Rak fusion protein used in Lanes 2–5 to produce fusion protein RakΔ86. This fusion protein was incubated with immunoprecipitated CDC2, and subjected to an in vitro kinase assay with Histone H1 added as an exogenous substrate, and analyzed by SDS-PAGE. A 1:2 serial dilution of the RakΔ86 fusion protein is shown in FIG. 7, lanes 6–9.

These results indicate that Rak associates with Cdc2 and Cdk4 through distinct sites, and that Rak may play a role in regulation of cell growth through interactions with cell cycle-associated kinases.

EXAMPLE 9

The CDC2 binding domain of RAK appears to be between amino acids 86–110. Since the binding of RAK to CDC2 is exceptionally strong, the biological function of this interaction was explored. The RAK-SH3:GST chimeric protein was able to block CDC2 histone H1 activity, whereas the SH3 deletion mutant lacking the 24 amino acid (SEQ ID NO:3) CDC2 binding site (RAKΔ86:GST) had greatly diminished CDC2 inhibitory activity. Using an 11 amino acid peptide (SEQ ID NO:4; KRRDGSSQQLQ) from within the 24 amino acid inhibitory domain, CDC2 histone H1 activity has been reproducibly attenuated in vitro.

These results indicate that domains of the RAK protein can be used to block CDC2 activity necessary for completion of the cell cycle.

That which is claimed is:

1. A peptide selected from the group consisting of
   a peptide of amino acid sequence (Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser) (SEQ ID NO:3); and
   a peptide of amino acid sequence (Lys-Arg-Arg-Asp-Gly-Ser-Ser-Gln-Gln-Leu-Gln) (SEQ ID NO:4).

2. An isolated DNA sequence encoding a peptide according to claim 1.

3. A vector comprising isolated DNA according to claim 2.

4. A host cell containing a vector according to claim 3.

5. A host cell containing a vector according to claim 3 and capable of expressing the same.

6. A fusion protein consisting of a protein and a peptide, said peptide selected from the group consisting of:
   a peptide of amino acid sequence (Lys-Arg-Arg-Asp-Gly-Ser-Ser-Gln-Gln-Leu-Gln-Gly-Tyr-Ile-Pro-Ser-Asn-Tyr-Val-Ala-Glu-Asp-Arg-Ser) (SEQ ID NO:3); and
   a peptide of amino acid sequence (Lys-Arg-Arg-Asp-Gly-Ser-Ser-Gln-Gln-Leu-Gln) (SEQ ID NO:4).

7. A fusion protein according to claim 6, wherein said protein is selected from the group consisting of beta-galactosidase, maltose binding protein, and glutathione-S-transferase.

8. A fusion protein according to claim 6, wherein said protein is glutathione-S-transferase.

* * * * *

UNITED STATES PATENT AND TRADEMARK OFFICE
CERTIFICATE OF CORRECTION

PATENT NO.    : 6,531,296 B1                                  Page 1 of 1
DATED         : March 11, 2003
INVENTOR(S)   : Liu et al.

It is certified that error appears in the above-identified patent and that said Letters Patent is hereby corrected as shown below:

<u>Title page,</u>
Item [75], Inventors, the residence of Inventor "Cance" should be listed as
-- Chapel Hill, North Carolina --.
Item [56], References Cited, OTHER PUBLICATIONS, the "Craven" reference should read as follows:

-- Craven et al.; The src-related nuclear tyrosine kinase rak associates with Rb, cyclin D3 and p34, AACR abstract 36:A3357 (1995). --

Signed and Sealed this

Twenty-eighth Day of October, 2003

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 2827 base pairs
        (B) TYPE: nucleic acid
        (C) STRANDEDNESS: single -continued

```
        (D) TOPOLOGY: linear (ii) MOLECULE TYPE: cDNA (ix) FEATURE:
        (A) NAME/KEY: CDS
        (B) LOCATION: 410..1924

(xi) SEQUENCE DESCRIPTION: SEQ ID NO:1:

TTTTAATTTT ATTTTATTTT TGTTGTGGGA TTCTTAAGCA GATAAGAAGA AAAGACACCT      60

TCCTAGTGAG CAGCTGCCCA GCTCCTGCTC AGTTTTGCCT CGGGGTAGCA CCTCCAGCCA     120

CAGAAAGCAA GCCGGTAAGT CTCTCCAGGT AGGACTTGCT GCAACCCCAG CTCCTGCTCA     180

GTTTTGCCTC GGGGTTAGCA CCTTCCAGCC ACAGAACGAA GCCGGTAGTC TCTCAGTAGA     240

CTTGGTGCAA CCCAGCTGCT GGACTGATCT GAAACGGACT TTGCATACTC TCCGAAGTAT     300

GGTGAGTTGG TGCTGACTTC AAAGTTGCCT GGTGAACCAA GATAAGGTGG ATCGCAGAGA     360

CTAAGGGGAG AGGGAGAAGC CCTGCTCCTC TTCTCCCCAC CAAGGCACA ATG AGC        415
                                                         Met Ser
                                                           1

AAC ATC TGT CAG AGG CTC TGG GAG TAC CTA GAA CCC TAT CTC CCC TGT      463
Asn Ile Cys Gln Arg Leu Trp Glu Tyr Leu Glu Pro Tyr Leu Pro Cys
          5                  10                  15

TTG TCC ACG GAG GCA GAC AAG TCA ACC GTG ATT GAA AAT CCA GGG GCC      511
Leu Ser Thr Glu Ala Asp Lys Ser Thr Val Ile Glu Asn Pro Gly Ala
     20                  25                  30

CTT TGC TCT CCC CAG TCA CAG AGG CAT GGC CAC TAC TTT GTC GCT TTG      559
Leu Cys Ser Pro Gln Ser Gln Arg His Gly His Tyr Phe Val Ala Leu
 35                  40                  45                  50

TTT GAT TAC CAC GCT CCG ACT GCT GAG GAG TTG AGC TTC CGA GCA GGT      607
Phe Asp Tyr His Ala Pro Thr Ala Glu Glu Leu Ser Phe Arg Ala Gly
                 55                  60                  65

GAC AAA CTT CAA GTT CTG GAC ACT TTG CAT GAG GGC TGG TGG TTT GCC      655
Asp Lys Leu Gln Val Leu Asp Thr Leu His Glu Gly Trp Trp Phe Ala
             70                  75                  80

AGA CAC TTG GAG AAA AGA CGA GAT GGC TCC AGT CAG CAA CTA CAA GGC      703
Arg His Leu Glu Lys Arg Arg Asp Gly Ser Ser Gln Gln Leu Gln Gly
         85                  90                  95

TAT ATT CCT TCT AAC TAC GTG GCT GAG GAC AGA AGC CTA CAG GCA GAG      751
Tyr Ile Pro Ser Asn Tyr Val Ala Glu Asp Arg Ser Leu Gln Ala Glu
100                 105                 110

GCG TGG TTC TTT GGA GCA ATC AGA AGA TCA GAT GCA GAG AAA CAA CTA      799
Ala Trp Phe Phe Gly Ala Ile Arg Arg Ser Asp Ala Glu Lys Gln Leu
115                 120                 125                 130

TTA TAT TCA GAA AAC AAG ACC GGT TCC TTT CTA ATC AGA GAA AGT GAA      847
Leu Tyr Ser Glu Asn Lys Thr Gly Ser Phe Leu Ile Arg Glu Ser Glu
                135                 140                 145

AGC CAA AAA GGA GAA TTC TCT CTT TCA GTT TTA GAT GGA GCA GTT GTA      895
Ser Gln Lys Gly Glu Phe Ser Leu Ser Val Leu Asp Gly Ala Val Val
            150                 155                 160

AAA CAC TAC AGA ATT AAA AGA CTG GAT GAA GGG GGA TTT TTT CTC ACG      943
Lys His Tyr Arg Ile Lys Arg Leu Asp Glu Gly Gly Phe Phe Leu Thr
        165                 170                 175

CGA AGA AGA ATC TTT TCA ACA CTG AAC GAA TTT GTG AGC CAC TAC ACC      991
Arg Arg Arg Ile Phe Ser Thr Leu Asn Glu Phe Val Ser His Tyr Thr
    180                 185                 190

AAG ACA AGT GAC GGC CTG TGT GTC AAG CTG GGA AAA CCA TGC TTA AAG     1039
Lys Thr Ser Asp Gly Leu Cys Val Lys Leu Gly Lys Pro Cys Leu Lys
195                 200                 205                 210

ATC CAG GTC CCA GCT CCA TTT GAT TTG TCG TAT AAA ACC GTG GAC CAA     1087
```

```
                                                      -continued

Ile Gln Val Pro Ala Pro Phe Asp Leu Ser Tyr Lys Thr Val Asp Gln
            215                 220                 225

TGG GAG ATA GAC CGC AAC TCC ATA CAG CTT CTG AAG CGA TTG GGA TCT      1135
Trp Glu Ile Asp Arg Asn Ser Ile Gln Leu Leu Lys Arg Leu Gly Ser
            230                 235                 240

GGT CAG TTT GGC GAA GTA TGG GAA GGT CTG TGG AAC AAT ACC ACT CCA      1183
Gly Gln Phe Gly Glu Val Trp Glu Gly Leu Trp Asn Asn Thr Thr Pro
            245                 250                 255

GTA GCA GTG AAA ACA TTA AAA CCA GGT TCA ATG GAT CCA AAT GAC TTC      1231
Val Ala Val Lys Thr Leu Lys Pro Gly Ser Met Asp Pro Asn Asp Phe
            260                 265                 270

CTG AGG GAG GCA CAG ATA ATG AAG AAC CTA AGA CAT CCA AAG CTT ATC      1279
Leu Arg Glu Ala Gln Ile Met Lys Asn Leu Arg His Pro Lys Leu Ile
275                 280                 285                 290

CAG CTT TAT GCT GTT TGC ACT TTA GAA GAT CCA ATT TAT ATT ATT ACA      1327
Gln Leu Tyr Ala Val Cys Thr Leu Glu Asp Pro Ile Tyr Ile Ile Thr
                295                 300                 305

GAG TTG ATG AGA CAT GGA AGT CTG CAA GAA TAT CTC CAA AAT GAC ACT      1375
Glu Leu Met Arg His Gly Ser Leu Gln Glu Tyr Leu Gln Asn Asp Thr
            310                 315                 320

GGA TCA AAA ATC CAT CTG ACT CAA CAG GTA GAC ATG GCG GCA CAG GTT      1423
Gly Ser Lys Ile His Leu Thr Gln Gln Val Asp Met Ala Ala Gln Val
            325                 330                 335

GCC TCT GGA ATG GCC TAT CTG GAG TCT CGG AAC TAC ATT CAC AGA GAT      1471
Ala Ser Gly Met Ala Tyr Leu Glu Ser Arg Asn Tyr Ile His Arg Asp
            340                 345                 350

CTG GCT GCC AGA AAT GTC CTC GTT GGT GAA CAT AAT ATC TAC AAA GTA      1519
Leu Ala Ala Arg Asn Val Leu Val Gly Glu His Asn Ile Tyr Lys Val
355                 360                 365                 370

GCA GAT TTT GGA CTT GCC AGA GTT TTT AAG GTA GAT AAT GAA GAC ATC      1567
Ala Asp Phe Gly Leu Ala Arg Val Phe Lys Val Asp Asn Glu Asp Ile
            375                 380                 385

TAT GAA TCA AGA CAC GAA ATA AAG CTA CCG GTG AAG TGG ACT GCG CCC      1615
Tyr Glu Ser Arg His Glu Ile Lys Leu Pro Val Lys Trp Thr Ala Pro
            390                 395                 400

GAA GCC ATT CGT AGT AAT AAA TTC AGC ATT AAG TCC GAT GTA TGG TCA      1663
Glu Ala Ile Arg Ser Asn Lys Phe Ser Ile Lys Ser Asp Val Trp Ser
            405                 410                 415

TTT GGA ATC CTT CTT TAT GAA ATC ATT ACT TAT GGC AAA ATG CCT TAC      1711
Phe Gly Ile Leu Leu Tyr Glu Ile Ile Thr Tyr Gly Lys Met Pro Tyr
            420                 425                 430

AGT GGT ATG ACA GGT GCC CAG GTA ATC CAG ATG TTG GCT CAA AAC TAT      1759
Ser Gly Met Thr Gly Ala Gln Val Ile Gln Met Leu Ala Gln Asn Tyr
435                 440                 445                 450

AGA CTT CCG CAA CCA TCC AAC TGT CCA CAG CAA TTT TAC AAC ATC ATG      1807
Arg Leu Pro Gln Pro Ser Asn Cys Pro Gln Gln Phe Tyr Asn Ile Met
            455                 460                 465

TTG GAG TGC TGG AAT GCA GAG CCT AAG GAA CGA CCT ACA TTT GAG ACA      1855
Leu Glu Cys Trp Asn Ala Glu Pro Lys Glu Arg Pro Thr Phe Glu Thr
            470                 475                 480

CTG CGT TGG AAA CTT GAA GAC TAT TTT GAA ACA GAC TCT TCA TAT TCA      1903
Leu Arg Trp Lys Leu Glu Asp Tyr Phe Glu Thr Asp Ser Ser Tyr Ser
            485                 490                 495

GAT GCA AAT AAC TTC ATA AGA TGAACACTGG AGAAGAATAT CAAATAATAA         1954
Asp Ala Asn Asn Phe Ile Arg
            500                 505

AGTAGCAAAA CAAATTCAAA TAATAATCCA TTCCAAAATA CAATGTTATC AACCAACTGC    2014

ACAATCAGTT TATCCTGACA TATTCAAGTG ATAGGATAAA GTTGGCCATG TATTATGAAA    2074
```

-continued

```
AAGATTATTT GTGCATTTTA TTGACTGGGC AACACTGCAG GACAGTCAAG GTGATATATA    2134

ATTTCCTCAC TGCCTGGTAA AATTAAGCAC ACTAAACCAA GTTATTTTTC TTTTTAAGAG    2194

ATACTTACAT TTCCATTTAT TGTTTGAAAT GTCGATCAAG AGAATCAACA GATGATAGTC    2254

CAATTTTTAC TCAGTGACTG TTGTAGCATT TTCCTGTTTA CTGATTAGAG TGGTTATCAT    2314

TATTCCTCAG ATTGCTGAAT CCCATCAGGC TGTTATTATG AAGGAATTTG ATTGCTTTGC    2374

TGCACAGCAG GACCTGTGCT TTGAGATTTT TTTTTCTCTT TTAAAATATC CTGTAACTAC    2434

AATGATGGTA AAGCCATGTT AAATGACTTG ATTGTACTTG GAGTAATTGC ACATTTTTTT    2494

TCTATGCATA AAAAAATGAT GCAGCTGTTG AGAAAACGAA GTCTTTTTCA TTTTGCAGAA    2554

GGAAATGATG GAATTTTTCT GTACTTCAGT ATGTGTCAAC TGAGAGTCAT ATACATTAGT    2614

TTTAATCTCT TAATATTGAG AATCAGGTTG CAAACGGATG AGTTATTATC TATGAAATGT    2674

GAGAAATGTC TAATAGCCCA TAAGTCTGAG AAATAGGTAT CAAAATAGTT TAGGAAAATG    2734

AGAGGAGAAC AGTAGGATTG CTGTGGCCTA GACTTCTGGT AATTAATAAA GAAAAGAAG    2794

TACCCTTTGG CCTACAAAAA AAAAAAAAAA AAG                                2827

(2) INFORMATION FOR SEQ ID NO:2:

(i) SEQUENCE CHARACTERISTICS:
        (A) LENGTH: 505 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Asn Ile Cys Gln Arg Leu Trp Glu Tyr Leu Glu Pro Tyr Leu
 1               5                  10                  15

Pro Cys Leu Ser Thr Glu Ala Asp Lys Ser Thr Val Ile Glu Asn Pro
            20                  25                  30

Gly Ala Leu Cys Ser Pro Gln Ser Gln Arg His Gly His Tyr Phe Val
        35                  40                  45

Ala Leu Phe Asp Tyr His Ala Pro Thr Ala Glu Glu Leu Ser Phe Arg
    50                  55                  60

Ala Gly Asp Lys Leu Gln Val Leu Asp Thr Leu His Glu Gly Trp Trp
65                  70                  75                  80

Phe Ala Arg His Leu Glu Lys Arg Arg Asp Gly Ser Ser Gln Gln Leu
                85                  90                  95

Gln Gly Tyr Ile Pro Ser Asn Tyr Val Ala Glu Asp Arg Ser Leu Gln
            100                 105                 110

Ala Glu Ala Trp Phe Phe Gly Ala Ile Arg Arg Ser Asp Ala Glu Lys
        115                 120                 125

Gln Leu Leu Tyr Ser Glu Asn Lys Thr Gly Ser Phe Leu Ile Arg Glu
    130                 135                 140

Ser Glu Ser Gln Lys Gly Glu Phe Ser Leu Ser Val Leu Asp Gly Ala
145                 150                 155                 160

Val Val Lys His Tyr Arg Ile Lys Arg Leu Asp Glu Gly Gly Phe Phe
                165                 170                 175

Leu Thr Arg Arg Arg Ile Phe Ser Thr Leu Asn Glu Phe Val Ser His
            180                 185                 190

Tyr Thr Lys Thr Ser Asp Gly Leu Cys Val Lys Leu Gly Lys Pro Cys
        195                 200                 205

Leu Lys Ile Gln Val Pro Ala Pro Phe Asp Leu Ser Tyr Lys Thr Val
    210                 215                 220
```

-continued

```
Asp Gln Trp Glu Ile Asp Arg Asn Ser Ile Gln Leu Leu Lys Arg Leu
225                 230                 235                 240

Gly Ser Gly Gln Phe Gly Glu Val Trp Glu Gly Leu Trp Asn Asn Thr
            245                 250                 255

Thr Pro Val Ala Val Lys Thr Leu Lys Pro Gly Ser Met Asp Pro Asn
                260                 265                 270

Asp Phe Leu Arg Glu Ala Gln Ile Met Lys Asn Leu Arg His Pro Lys
            275                 280                 285

Leu Ile Gln Leu Tyr Ala Val Cys Thr Leu Glu Asp Pro Ile Tyr Ile
    290                 295                 300

Ile Thr Glu Leu Met Arg His Gly Ser Leu Gln Glu Tyr Leu Gln Asn
305                 310                 315                 320

Asp Thr Gly Ser Lys Ile His Leu Thr Gln Gln Val Asp Met Ala Ala
                325                 330                 335

Gln Val Ala Ser Gly Met Ala Tyr Leu Glu Ser Arg Asn Tyr Ile His
            340                 345                 350

Arg Asp Leu Ala Ala Arg Asn Val Leu Val Gly Glu His Asn Ile Tyr
        355                 360                 365

Lys Val Ala Asp Phe Gly Leu Ala Arg Val Phe Lys Val Asp Asn Glu
    370                 375                 380

Asp Ile Tyr Glu Ser Arg His Glu Ile Lys Leu Pro Val Lys Trp Thr
385                 390                 395                 400

Ala Pro Glu Ala Ile Arg Ser Asn Lys Phe Ser Ile Lys Ser Asp Val
                405                 410                 415

Trp Ser Phe Gly Ile Leu Leu Tyr Glu Ile Thr Tyr Gly Lys Met
            420                 425                 430

Pro Tyr Ser Gly Met Thr Gly Ala Gln Val Ile Gln Met Leu Ala Gln
        435                 440                 445

Asn Tyr Arg Leu Pro Gln Pro Ser Asn Cys Pro Gln Gln Phe Tyr Asn
    450                 455                 460

Ile Met Leu Glu Cys Trp Asn Ala Glu Pro Lys Glu Arg Pro Thr Phe
465                 470                 475                 480

Glu Thr Leu Arg Trp Lys Leu Glu Asp Tyr Phe Glu Thr Asp Ser Ser
                485                 490                 495

Tyr Ser Asp Ala Asn Asn Phe Ile Arg
            500                 505
```

(2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Lys Arg Arg Asp Gly Ser Ser Gln Gln Leu Gln Gly Tyr Ile Pro Ser
1               5                   10                  15

Asn Tyr Val Ala Glu Asp Arg Ser
            20
```

(2) INFORMATION FOR SEQ ID NO:4:

(i) SEQUENCE CHARACTERISTICS:
        (A) LENGTH: 11 amino acids

```
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Lys Arg Arg Asp Gly Ser Ser Gln Gln Leu Gln
1               5                   10

(2) INFORMATION FOR SEQ ID NO:5:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

CCTTCCTGGG CATGGAGTCC TG                                              22

(2) INFORMATION FOR SEQ ID NO:6:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

GGACAATGAT CTTGATCTTC                                                 20

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

CGGATCCCAG ATGTTCGCTC                                                 20

(2) INFORMATION FOR SEQ ID NO:8:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:8:

GAAGCTTAGT AGAATACTTC AA                                              22

(2) INFORMATION FOR SEQ ID NO:9:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

(ii) MOLECULE TYPE: cDNA (xi) SEQUENCE DESCRIPTION: SEQ ID NO:9:

GCTCAAAACT TTAGACTTCC                                                    20

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

ACAGCAATTT TTCAACATCA                                                    20

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

TGAAGACTTT TTTGAAACAG                                                    20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

ACTCTTCATT TTCAGATGCA                                                    20

(2) INFORMATION FOR SEQ ID NO:13:

(i) SEQUENCE CHARACTERISTICS:
            (A) LENGTH: 46 amino acids
            (B) TYPE: amino acid
            (D) TOPOLOGY: linear (ii) MOLECULE TYPE: protein (xi) SEQUENCE DESCRIPTION: SEQ ID NO:13:

Met Ser Asn Ile Cys Gln Arg Leu Trp Glu Tyr Leu Glu Pro Tyr Leu
 1               5                  10                  15

Pro Cys Leu Ser Thr Glu Ala Asp Lys Ser Thr Val Ile Glu Asn Pro
                20                  25                  30

Gly Ala Leu Cys Ser Pro Gln Ser Gln Arg His Gly His Tyr
                35                  40                  45